(12) United States Patent
Mchale et al.

(10) Patent No.: US 11,235,000 B2
(45) Date of Patent: Feb. 1, 2022

(54) CALCIUM PEROXIDES NANOPARTICLES AS ADJUVANT THERAPY

(71) Applicant: UNIVERSITY OF ULSTER, Antrim (GB)

(72) Inventors: Anthony Mchale, Ballycastle Antrim (GB); John Callan, Ballycastle Antrim (GB); Yingjie Sheng, Coleraine Londonderry (GB)

(73) Assignee: UNIVERSITY OF ULSTER, Antrim (GB)

( * ) Notice: Subject to any disclaimer, the term of this patent is extended or adjusted under 35 U.S.C. 154(b) by 0 days.

(21) Appl. No.: 16/610,151

(22) PCT Filed: May 4, 2018

(86) PCT No.: PCT/GB2018/051207
§ 371 (c)(1),
(2) Date: Nov. 1, 2019

(87) PCT Pub. No.: WO2018/203083
PCT Pub. Date: Nov. 8, 2018

(65) Prior Publication Data
US 2020/0069727 A1 Mar. 5, 2020

(30) Foreign Application Priority Data
May 4, 2017 (GB) .................................. 1707153

(51) Int. Cl.
| | | |
|---|---|---|
| A61K 31/78 | (2006.01) | |
| A61K 47/69 | (2017.01) | |
| A61P 35/00 | (2006.01) | |
| A61K 9/00 | (2006.01) | |
| A61K 9/51 | (2006.01) | |
| A61K 41/00 | (2020.01) | |
| A61K 47/02 | (2006.01) | |

(52) U.S. Cl.
CPC ............ *A61K 31/78* (2013.01); *A61K 9/0019* (2013.01); *A61K 9/5115* (2013.01); *A61K 41/0033* (2013.01); *A61K 41/0038* (2013.01); *A61K 41/0047* (2013.01); *A61K 41/0057* (2013.01); *A61K 47/02* (2013.01); *A61K 47/6923* (2017.08); *A61K 47/6929* (2017.08); *A61P 35/00* (2018.01)

(58) Field of Classification Search
None
See application file for complete search history.

(56) References Cited

U.S. PATENT DOCUMENTS

| | | |
|---|---|---|
| 4,470,839 A | 9/1984 | Gago |
| 2002/0051744 A1 | 5/2002 | Doetsch et al. |
| 2002/0098246 A1 | 7/2002 | Howes |
| 2009/0169630 A1 | 7/2009 | Ward et al. |
| 2009/0324668 A1 | 12/2009 | Kangasniemi et al. |
| 2010/0112087 A1 | 5/2010 | Harrison et al. |
| 2010/0119608 A1 | 5/2010 | Chung |
| 2012/0114729 A1 | 5/2012 | Stabler et al. |
| 2012/0251450 A1 | 10/2012 | Punnoose et al. |
| 2014/0322342 A1 | 10/2014 | Opara et al. |
| 2016/0114145 A1 | 4/2016 | Cook et al. |
| 2016/0228380 A1 | 8/2016 | McHugh et al. |

FOREIGN PATENT DOCUMENTS

| | | |
|---|---|---|
| AU | 2013203151 | 5/2013 |
| CN | 103964395 | 8/2014 |
| CN | 104629092 | 5/2015 |
| CN | 104840484 | 8/2015 |
| EP | 2 741 775 | 1/2017 |
| WO | 2008/000888 | 1/2008 |

OTHER PUBLICATIONS

Newland et al. "Oxygen-Producing Gellan Gum Hydrogels for Dual Delivery of Either Oxygen or Peroxide with Doxorubicin", ACS Biomater. Sci. Eng. 2017, 3, 5, 787-792. (Year: 2017).*
International Search Report And Written Opinion Of The International Searching Authority dated Nov. 6, 2018 in International (PCT) Application No. PCT/GB2018/051207.
International Preliminary Report On Patentability dated Nov. 14, 2019 in International (PCT) Application No. PCT/GB2018/051207.
Search Report dated Feb. 28, 2018 in United Kingdom Patent Application No. GB1707153.1.
Huang et al., "An Implantable Depot That Can Generate Oxygen in Situ for Overcoming Hypoxia-Induced Resistance to Anticancer Drugs in Chemotherapy," J. Am. Chem. Soc., 2016, 138:272-285.
Sheng et al., "Oxygen generating nanoparticles for improved photodynamic therapy of hypoxic tumours," Journal of Controlled Release, Oct. 2017, vol. 264, pp. 333-340.
Liu et al., "Dual-Stage Light Amplified Photodynamic Therapy against Hypoxic Tumor Based on an $O_2$ Self-Sufficient Nanoplatform" Small, Oct. 2017, vol. 13, Issue 37, pp. 1-3.
Khodaveisi et al., "Synthesis of calcium peroxide nanoparticles as an innovative reagent for in situ chemical oxidation," Journal of Hazardous Materials, 2011, vol. 192, pp. 1437-1440.
Abdi et al., "An enzyme-modulated oxygen-producing microsystem for regenerative therapeutics," International Journal of Pharmaceutics, 2011, vol. 409, pp. 203-205.

* cited by examiner

*Primary Examiner* — Melissa L Fisher
(74) *Attorney, Agent, or Firm* — Wenderoth, Lind & Ponack, L.L.P.

(57) ABSTRACT

The invention provides $CaO_2$ nanoparticles having a pH-responsive coating for use in a method of adjuvant therapy of hypoxic tumour cells or tissues. The nanoparticles find particular use in enhancing cancer therapies that depend on oxygen to exert their effect, such as photodynamic therapy (PDT), sonodynamic therapy (SDT), and radiotherapy. The invention also provides pharmaceutical compositions containing the coated $CaO_2$ nanoparticles, together with at least one photosensitiser, sonosensitiser, or radiosensitiser and, optionally, at least one pharmaceutical carrier or excipient.

20 Claims, 7 Drawing Sheets

(a)

(b)

(a)

(b)

(a)

(b)

(a)

(b)

CALCIUM PEROXIDES NANOPARTICLES AS ADJUVANT THERAPY

TECHNICAL FIELD

The present invention relates to the use of modified calcium peroxide ($CaO_2$) nanoparticles for the targeted delivery of active oxygen to hypoxic cells and tissues. More specifically, it relates to the use of pH-responsive $CaO_2$ nanoparticles which are capable of oxygenating tissues in which a pH gradient exists.

Such nanoparticles find particular use in enhancing the efficacy of therapeutic methods which rely on the presence of oxygen. For example, these may be used to improve the oxygenation of hypoxic tumours thereby enhancing cancer therapies that depend on oxygen to exert their effect, such as photodynamic therapy (PDT), sonodynamic therapy (SDT), and radiotherapy.

BACKGROUND OF THE INVENTION

PDT is a clinically approved cancer treatment that involves irradiating a photoactive drug with light, which in the presence of molecular oxygen, generates toxic levels of reactive oxygen species (ROS) ultimately resulting in cell death (Yano et al., Journal of Photochemistry and Photobiology C: Photochemistry Reviews, 12(1): 46-67, 2011). By carefully controlling light delivery to the target lesion, ROS generation can be localised with high precision in three dimensions sparing healthy surrounding tissue. While the targeted nature of PDT remains its greatest attraction, the technique is significantly limited by the inability of light to penetrate deeply through human tissue (Cui et al., ACS nano, 7(1): 676-688, 2012). This has restricted PDT to the treatment of superficial lesions and hindered its ability to treat larger solid tumours.

The development of near-infrared (NIR) absorbing sensitisers and the emergence of sonodynamic therapy (SDT) promise to overcome this limitation by enabling the activation of sensitisers at greater depths in vivo (Taratula et al., Molecular Pharmaceutics, 10(10): 3946-3958, 2013).

SDT involves the combination of ultrasound and a sono-sensitising drug. In a manner similar to PDT, activation of the sonosensitiser by acoustic energy results in the generation of reactive oxygen species (ROS), such as singlet oxygen, at the target site of interest. Such species are cytotoxic, thereby killing the target cells or at least diminishing their proliferative potential. Many known photosensitising agents can be activated by acoustic energy and are thus suitable for use in SDT. Since ultrasound readily propagates through several cm of tissue, SDT provides a means by which tumours which are located deep within the tissues may be treated. As with light, ultrasound energy can also be focused on a tumour mass in order to activate the sonosenitiser thereby restricting its effects to the target site.

Oxygen is a key requirement for the generation of ROS in both PDT and SDT. Combatting hypoxia thus represents a major challenge in the treatment of solid tumours using these therapies. This is particularly the case for tumours of the pancreas and hypoxia is now recognised as an indicator of poor prognosis for many types of cancer. Inefficient gas and mass transfer resulting from atypical vascularisation as well as oxygen demand by hyper-proliferating tissues results in hypoxia in most solid tumours. Once a hypoxic environment develops in the tumour, cell populations become resistant to many conventional cancer chemotherapeutic agents through a variety of adaptive survival mechanisms.

Similarly, for radiotherapy, oxygen has been shown to play a very significant role in enhancing radiation induced damage to nucleic acid in target tissues. One of the major challenges associated with the latter has been to provide oxygen to the target tissues during therapy. A number of approaches have been employed including hyperbaric oxygen breathing and breathing pure oxygen or carbogen at atmospheric pressure. Such approaches, however, have delivered limited success.

Recently, the inventors have shown that the selective destruction of oxygen loaded microbubbles in the tumour microenvironment using low intensity ultrasound provides a temporary boost in tumour oxygen levels which enhances SDT treatment of pancreatic tumours (see McEwan et al., Biomaterials, 80: 20-32, 2016). However, a need still exists for alternative methods for the treatment of hypoxic tumours, in particular for the treatment of pancreatic cancer. The present invention addresses this need.

SUMMARY OF THE INVENTION

The inventors now propose the use of in-situ oxygen generating nanoparticles in an alternative method to improve tumour oxygenation in cancer therapies which are reliant on the presence of oxygen in the tumour tissues to be effective. Such nanoparticles may be used as an effective adjuvant to therapies such as PDT and/or SDT, and in radiotherapy in which oxygen plays a key role in inducing damage to target tissues.

Specifically, the inventors propose the use of calcium peroxide ($CaO_2$) nanoparticles (NPs) provided with a pH-responsive coating to enable the controlled generation of molecular oxygen as a function of pH. Tumour interstitial fluid is more acidic (pH=6.0) than normal tissue as hypoxia generates an over-production of acid by inducing the production of energy from glycolysis via the Pasteur effect (Fang et al., Seminars in cancer biology, Elsevier, pages 330-337, 2008). It is proposed that this difference in pH is used to provide a pH-responsive delivery of oxygen directly to the tumour site.

Calcium peroxide rapidly decomposes in the presence of moisture to produce active oxygen according to the following equation:

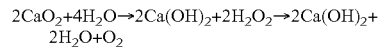

$$2CaO_2 + 4H_2O \rightarrow 2Ca(OH)_2 + 2H_2O_2 \rightarrow 2Ca(OH)_2 + 2H_2O + O_2$$

This decomposition is accelerated in the presence of acid.

Coating of the $CaO_2$ nanoparticles as herein described protects these from decomposition whilst in systemic circulation in the blood and normal tissues (e.g. at pH values of 7.4 and above), but enables their 'activation' in the more acidic tumour tissues. The resulting oxygen generation improves oxygenation in the hypoxic environment of the tumour and enhances cancer therapies, such as PDT and SDT treatments, and also radiotherapy.

Embodiments of the invention are illustrated herein by way of suitable examples for the preparation and characterisation of $CaO_2$ nanoparticles ($CaO_2$ NPs) that generate molecular oxygen upon decomposition in water.

In one embodiment of the invention, the nanoparticles are coated with a pH-responsive methacrylate-based copolymer containing a tertiary amine residue that protects the nanoparticle core from water at pH values above about 7.4. At lower pH values, the tertiary amine unit ionises resulting in dissolution of the polymer coating and exposure of the nanoparticle core to the aqueous environment resulting in oxygen generation. In the examples presented herein, the oxygen generating capability of the polymer coated $CaO_2$ NPs is demonstrated in aqueous solution. Minimal oxygen was produced at pH 7.4 but when the pH was reduced to 6.2 this increased significantly.

The ability of the resulting oxygen generation to improve oxygenation in hypoxic environments and enhance the PDT treatment of BxPC-3 pancreatic cancer cells in vitro and human xenograft Mia-Paca-2 tumours in vivo is also demonstrated in the examples presented herein. Specifically, polymer coated $CaO_2$ NPs are shown to significantly increase tumour $pO_2$ levels ($p<0.05$) in mice bearing ectopic human xenograft MiaPaCa-2 tumours with an average increase in tumour $pO_2$ of 6.5 mmHg in the period 10 to 30 minutes following administration. A statistically significant improvement in PDT mediated efficacy ($p<0.001$) is also shown when the particles are administered to mice bearing the same tumours 20 minutes prior to PDT treatment.

The results presented herein provide evidence that the polymer coated $CaO_2$ nanoparticle formulation has great potential as an in situ method for oxygen generation to enhance the efficacy of treatments, such as PDT, SDT and radiotherapy, which depend on oxygen to exert their cytotoxic effects.

In its broadest aspect the invention relates to $CaO_2$ nanoparticles having a pH-responsive coating for use in a method of adjuvant therapy of hypoxic tumour cells or tissues.

Such nanoparticles find particular use as an adjuvant therapy to methods of photodynamic therapy, sonodynamic therapy, and radiotherapy which are reliant on the presence of molecular oxygen to exert their cytotoxic effects.

In another aspect the invention relates to a method of adjuvant therapy of hypoxic tumour cells or tissues in a patient, said method comprising the step of administering to said cells or tissues of said patient an effective amount of $CaO_2$ nanoparticles having a pH-responsive coating.

In a further aspect the invention relates to a method of treatment of hypoxic tumour cells or tissues in a patient, said method comprising the following steps:
(i) administering to said cells or tissues of said patient an effective amount of $CaO_2$ nanoparticles having a pH-responsive coating;
(ii) if required, administering to said cells or tissues of said patient at least one of the following active agents: a photosensitiser, a sonosensitiser, or a radiosensitiser; and
(iii) subjecting said cells or tissues to one or more of the following: light, ultrasound and ionising radiation whereby to treat said tumour cells or tissues.

Steps (i) and (ii) may be carried out simultaneously, or separately. Where these are carried out separately, these may be performed in any order although generally step (ii) will precede step (i).

In a further aspect the invention relates to the use of $CaO_2$ nanoparticles having a pH-responsive coating in the manufacture of a medicament for use in a method of adjuvant therapy of hypoxic tumour cells or tissues.

In a yet further aspect the invention relates to a pharmaceutical composition comprising $CaO_2$ nanoparticles having a pH-responsive coating, together with at least one photosensitiser, sonosensitiser, or radiosensitiser and, optionally, at least one pharmaceutical carrier or excipient.

In another aspect the invention relates to a product comprising (i) $CaO_2$ nanoparticles having a pH-responsive coating, and (ii) a photosensitiser, a sonosensitiser, or a radiosensitiser for simultaneous or sequential use in a method of photodynamic therapy, sonodynamic therapy, or radiotherapy.

In another aspect the invention relates to a kit comprising the following components: (i) $CaO_2$ nanoparticles having a pH-responsive coating, (ii) a photosensitiser, a sonosensitiser, or a radiosensitiser; and optionally (iii) instructions for the use of said components in a method of photodynamic therapy, sonodynamic therapy, or radiotherapy.

In another aspect the invention relates to $CaO_2$ nanoparticles having a pH-responsive coating, wherein said coating comprises (e.g. consists essentially of) a polymer obtainable (or obtained) by polymerisation of the following monomers: methyl methacrylate, ethyl acrylate and 2-(dimethylamino) ethyl methacrylate.

In another aspect the invention relates to $CaO_2$ nanoparticles having a pH-responsive coating, wherein said coating is linked to at least one of the following active agents: a photosensitiser, a sonosensitiser, a radiosensitiser, or an enzyme capable of catalysing the degradation of $H_2O_2$ to oxygen, e.g. catalase.

In another aspect the invention relates to a polymeric (nano)particle having embedded therein $CaO_2$ nanoparticles which optionally are provided with a pH-responsive coating, wherein said polymeric (nano)particle further comprises and/or is linked to one or more of the following active agents: a photosensitiser, a sonosensitiser, a radiosensitiser, or an enzyme capable of catalysing the degradation of $H_2O_2$ to oxygen, e.g. catalase.

The coated $CaO_2$ nanoparticles, polymeric (nano)particles, pharmaceutical compositions, methods and uses herein described are particularly suitable for use in methods for the treatment of hypoxic tumours, such as pancreatic cancer.

DETAILED DESCRIPTION OF THE INVENTION

Definitions

As used herein, the term "nanoparticle" refers to a solid particle having at least one dimension (e.g. a diameter) which is less than about 1 μm, preferably a particle having at least one dimension (e.g. a diameter) in the range from 5 to 900 nm, more preferably in the range from 10 to 500 nm, e.g. in the range from 10 to 300 nm.

Unless otherwise specified, the term "nanoparticle" is intended to refer to a $CaO_2$-containing nanoparticle without any coating.

It should be understood that the term "nanoparticle" does not imply any particular shape, but includes all known shapes including, but not limited to, a sphere, a rod, a wire, and any other substantially spherical shape such as an ovoid.

As used herein, the terms "calcium peroxide nanoparticle", "$CaO_2$ nanoparticle", and "$CaO_2$ NP" are used interchangeably and are intended to refer to a solid nanoparticle which comprises calcium peroxide. Other components other than calcium peroxide may be present. In some embodiments, the $CaO_2$ nanoparticle may consist essentially of calcium peroxide. In some embodiments, the $CaO_2$ nanoparticle may consist of calcium peroxide.

As used herein, the term "pH-responsive coating" refers to a coating which is stable under near neutral or physiological conditions, but which dissolves (partly or fully) at a pH below physiological pH, e.g. at a pH less than about 7.4.

As used herein, the term "adjuvant therapy" refers to the administration of a therapeutic agent in addition to the main treatment for the disease. In the context of the invention, the main treatment for such patients is cancer therapy and the disease is a hypoxic tumour. The adjuvant therapy according to the invention may be carried out simultaneously with the cancer therapy. Typically, however, this will be carried out prior to the cancer therapy.

As used herein, the term "photodynamic therapy" is intended to refer to a method involving the combination of light and either a photosensitiser, or a precursor of a photosensitiser, in which activation of the photosensitiser by light results in the generation of reactive oxygen species, such as singlet oxygen. The term "photosensitiser precursor" is intended to encompass any compound which is converted metabolically to a photosensitiser and is thus essentially equivalent thereto.

As used herein, the term "sonodynamic therapy" is intended to refer to a method involving the combination of ultrasound and a sonosensitiser in which activation of the sonosensitiser by acoustic energy results in the generation of reactive oxygen species, such as singlet oxygen.

As used herein, the terms "radiotherapy" and "radiation therapy" are intended to refer to a method involving the use of ionising radiation to control or kill tumour cells by damaging the DNA of the cells leading to cell death. Optionally, the method may involve the combined use of a radiosensitiser which renders the target tumour cells more sensitive to radiation therapy.

In one aspect the invention provides $CaO_2$ nanoparticles having a pH-responsive coating for use in a method of adjuvant therapy of hypoxic tumour cells or tissues.

In one embodiment, the coated nanoparticles may be used as an adjuvant therapy to photodynamic therapy, sonodynamic therapy, or radiation therapy.

$CaO_2$ for use in the invention is provided in nanoparticulate form. The $CaO_2$ is in a divided solid state, for example this may be provided in the form of a granulate or free flowing powder. Alternatively, this may be provided in the form of agglomerates of individual nanoparticles which are bound to one another. Such agglomerates may be considered "nanoparticles" as herein described.

$CaO_2$ nanoparticles suitable for use in the invention may have diameters of up to about 1 μm. For example, these may have diameters ranging from 5 to 900 nm, preferably in the range from 10 to 500 nm, more preferably in the range from 10 to 300 nm. In some embodiments, these may have diameters of less than about 100 nm, e.g. in the range from 0.5 nm to 100 nm, preferably from 1 nm to 50 nm, more preferably from 5 nm to 40 nm, e.g. from 10 nm to 30 nm.

The measurement of particle size and the preparation of $CaO_2$ having a given particle size may be performed using techniques known in the art and described herein. For example, particle sizes may be determined by optical analysis, laser diffraction, etc. Particle sizes are defined herein according to the size of particles which will typically pass through, and/or be retained by, conventional filters having a given mesh size. It will be understood that the $CaO_2$ nanoparticles herein described are typically anisotropic and non-uniform in nature and that filtration relates primarily to the maximum diameter of any nanoparticle. Methods and apparatus for separating particulates of the sizes defined herein are generally known in the art.

$CaO_2$ nanoparticles for use in the invention may contain other components besides $CaO_2$. The nature of any such components will be dependent on the method by which they are produced and may, for example, include unreacted reactants or by-products. Typically, the nanoparticles will contain at least 10 wt. %, preferably at least 15 wt. %, at least 20 wt. %, at least 25 wt. %, or at least 30 wt. %, or at least 40 wt. % of active $CaO_2$ (based on the total weight of the particles). In some embodiments, the nanoparticles will consist essentially of (e.g. consist of) calcium peroxide. Where other components are present, these should be physiologically tolerable, either by virtue of their composition and/or the amount in which they are present. The choice of method used for preparation of the nanoparticles should be selected accordingly. Where other components are present, these will generally be present in an amount of less than 70 wt. %, preferably less than 65 wt. %, more preferably less than 60 wt. % (based on the total weight of the particles). Methods for determining the content of calcium peroxide are known in the art, including methods such as that described in Example 2, as well as spectroscopic methods for the determination of elemental composition (e.g. atomic absorption spectrometry).

$CaO_2$ nanoparticles suitable for use in the invention may be prepared by known methods. These include hydrolysis of a suitable calcium salt, precipitation, milling (e.g. ball milling) or grinding, and combinations thereof.

In one embodiment, the $CaO_2$ nanoparticles for use in the invention may be produced by an oxidation-hydrolysis-precipitation procedure, for example as described by Khodaveiside et al. (Journal of Hazardous Materials, 192(3): 1437-1440, 2011). This method is generally suitable for the preparation of less stable peroxides, such as calcium peroxide, and involves precipitating the insoluble peroxide from an aqueous solution by adding $H_2O_2$ to a basic solution of the metal salt, such as calcium chloride:

$$CaCl_2 + H_2O_2 \rightarrow CaO_2(\text{hydrate}) + 2HCl$$

The addition of aqueous ammonia to neutralise the HCl forces the reaction to favour the precipitation of the peroxide hydrate. The addition of a surfactant, such as polyethylene glycol 200 (PEG200), serves to stabilise the nanoparticles by preventing their irreversible agglomeration.

The following method may, for example, be used to prepare the $CaO_2$ nanoparticles: a source of calcium (e.g. a salt such as calcium chloride) may be used as a suitable calcium precursor and is combined with a suitable surfactant (such as polyethylene glycol, e.g. PEG200) and aqueous ammonia. Following the addition of surfactant to the solution containing the Ca(II) ions (e.g. an aqueous solution of calcium chloride and ammonia), hydrogen peroxide is added to form calcium peroxide. The addition of a suitable base, such as NaOH, serves to increase the pH whereby to cause precipitation of the calcium peroxide. This may be separated from the solution by known separation methods, such as centrifugation. Generally, the resulting product will be washed (e.g. with further addition of base, e.g. NaOH). Following washing, the resulting powder may be dried using conventional drying techniques. For example, it may be dried in vacuo at a temperature in the range of 40 to 100° C., e.g. about 80° C. for 1 to 4 hours, e.g. about 2 hours. In order to produce particles having the desired particle size the product may be separated using known separation techniques. In one embodiment, a suspension of the particles in an organic solvent (e.g. ethanol) may be passed through a suitable filter in order to separate out larger sized particles. The filtrate may then be dried in order to provide the desired $CaO_2$ nanoparticles as a powder.

The oxidation-hydrolysis-precipitation procedure described above provides pure, stabilised nanoparticles of calcium peroxide. It is expected that these will generally be suitable for use in accordance with the invention without the need for further processing. However, if appropriate, the CaO₂ nanoparticles may be subjected to further treatment such as particle size alteration (e.g. by milling or grinding) to provide the desired nanoparticulate CaO₂ for use in the invention. Preparation of nanoparticles with given sizes may, for example, be achieved by crushing, milling, grinding, etc. optionally followed by filtration, sedimentation, centrifugation, etc.

As will be understood, the calcium peroxide nanoparticles for use in the invention should be suitable for use in vivo. For example, they should be substantially free from any non-physiologically tolerable substances.

For use in the invention the CaO₂ nanoparticles are modified by coating or substantially coating the nanoparticles with a pH-responsive coating which controls the accessibility of the CaO₂ within the core to moisture. The coating constitutes a layer, preferably a continuous layer, arranged around each particle. In some embodiments, more than one coating layer may be applied, but typically the coating will comprise a single layer.

Suitable coating materials are known in the art and include polymer materials which are stable at physiological pH but which degrade (e.g. dissolve) at a pH which is less than physiological pH, e.g. at a pH of less than about 7.4.

The pH-responsive coating provides for the controlled release of oxygen to the target cells or tissues. The pH of hypoxic tumours is typically in the region of about pH 6.2 to pH 6.8. The nanoparticles may therefore be provided with a pH-sensitive coating with a dissolution threshold in the range of pH 6.0 to 7.4, preferably 6.2 to 7.4.

pH-responsive coatings which destabilise and degrade at acidic pH are known in the art and include conventional enteric coatings known for use in oral pharmaceutical products or suitable derivatives of these. Materials known for use as enteric coatings and which may be used in the invention include any of the following: cellulose acetate, hydroxypropyl methylcellulose, copolymers of methacrylic acid and methacrylic esters, polyvinylacetophthalate, cellulose acetate phthalate (CAP), ethylcellulose, dibutyl phthalate and diethyl phthalate and suitable derivatives of such compounds.

Materials which are suitable for use as pH-responsive coatings will generally include one or more basic units which under acidic conditions become protonated (i.e. ionise) thereby resulting in dissolution of the polymer coating in the acidic environment of a tumour, e.g. at a pH less than about 7.4. Suitable basic units may readily be selected by those skilled in the art, but include any primary, secondary and tertiary amine groups. Examples of suitable basic units include, but are not limited to, any of the following: imidazole, pyridine, pyrimidine, piperidine, histidine, lysine, quinoline, isoquinoline, morpholine, pyrazine and pyrrolidine. Any of these basic units may be incorporated into any of the enteric coating materials mentioned above, either in the backbone of the polymer or, more preferably, these may be linked to the polymers to provide functional, basic side-chains using methods known in the art.

In one embodiment, the coating comprises a copolymer derived from esters of acrylic and methacrylic acid and which has suitable functional groups such as tertiary amine groups, for example a suitably funtionalised copolymer comprising ethylacrylate and methylmethacrylate. Examples of such materials are those sold as Eudragit® polymers. Such polymers are insoluble and their release profiles can be altered by varying mixing ratios and/or coating thickness. Suitable Eudragit® polymers which degrade under acidic conditions include the Eudragit® E-type polymers which are particularly suitable for use in the invention. Other polymers for use in the invention may be provided by replacing the basic tertiary amine unit in any of these polymer materials with any of the basic units mentioned herein.

In one embodiment the coating material is a copolymer derived from esters of acrylic acid and methacrylic acid in which at least one of the monomers is modified by the introduction of a suitable functional group or groups. Suitable functional groups are those which are present in substantially non-ionised (e.g. free base) form at physiological pH (e.g. at a pH of about 7.4) but which convert to an ionised form at a lower pH, for example at a pH in the range from 6.2 to 6.9. Due to their increased ionisation at lower pH these render the polymer material more soluble and thus degradable. Suitable functional groups can readily be determined by those skilled in the art. These include amines, e.g. tertiary amines.

Examples of suitable coating materials include the following ternary polymers of formula (I) prepared from the reaction of methyl methacrylate, ethyl acrylate and 2-(dimethylamino) ethyl methacrylate:

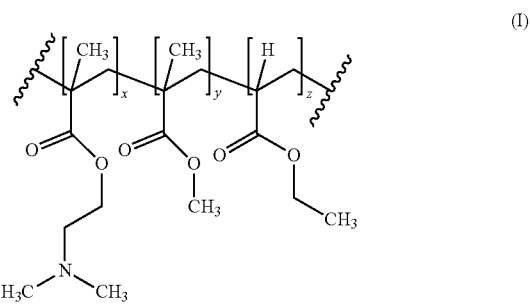

(I)

wherein x, y and z are integers representing the molar ratio of the monomeric units in the polymer material. In one embodiment, the ratio of x:y:z may be about 1:2:1.

CaO₂ nanoparticles coated with such polymer materials are in themselves novel and form a further aspect of the invention. In another aspect the invention thus provides CaO₂ nanoparticles having a pH-responsive coating, wherein said coating comprises (e.g. consists essentially of) a polymer obtainable (or obtained) by polymerisation of the following monomers: methyl methacrylate, ethyl acrylate and 2-(dimethylamino) ethyl methacrylate.

As will be described herein, any of the polymeric coating materials herein described (including those having the general structure of terpolymer (I) above) may be modified to include a further monomeric unit in the repeat-unit sequence having a side-chain which is bound to an enzyme (e.g. catalase), a sensitiser (e.g. a photosensitiser or a sonosensitiser), or a drug (e.g. a radiosensitiser).

In a further aspect the invention thus provides CaO₂ nanoparticles having a pH-responsive coating, wherein said coating is linked to at least one of the following active agents: a photosensitiser, a sonosensitiser, a radiosensitiser, or an enzyme capable of catalysing the degradation of H₂O₂ to oxygen, e.g. catalase.

Ternary polymers of formula (I), and suitably functionalised derivatives thereof, may be produced by conventional free radical co-polymerisation methods. Suitable free radical initiators include azobis(cyclohexanecarbonitrile) (ABCN). Other polymerisation methods may also be used in preparation of the polymer coatings, including anionic, cationic and photo-initiated polymerisations, in addition to step-growth polymerisations.

The pH-responsive coating may contain other additives such as other biocompatible polymer materials. Where these are present, these will generally be present in low amounts, for example these should not exceed 5 wt. % (based on the weight of the coating). The precise nature of the coating material, its thickness and/or the concentration of the components within the coating may be varied as required to obtain the desired oxygen release profile.

The pH-responsive coating may be applied to the nanoparticles using known coating methods, including but not limited to, solvent evaporation techniques, spray drying, dip coating, and oil-in-water emulsion techniques. In one embodiment, a modified single oil-in-water emulsion method may be used based on that described by Choi et al. (International Journal of Pharmaceutics, 311(1): 223-228, 2006). In this method the $CaO_2$ nanoparticles are dispersed in a suitable solvent (e.g. hexane) and sonicated for a period sufficient to provide a suspension of the particles (e.g. from 1 to 30 mins, e.g. about 5 mins). This suspension is then added dropwise to a solution of the coating polymer in a second solvent (e.g. ethanol) under conditions which ensure efficient mixing, e.g. using a homogeniser at 9000 RPM for 5 mins. Mixing is continued for a further period, for example up to about 6-8 hours, after which the resulting emulsion may be freeze dried. When required for use, this can be reconstituted, for example in sterile water or any other physiologically acceptable medium.

In one embodiment, the nanoparticles may be provided with more than one coating, for example a second polymer coating. For example, these may be embedded in other polymeric materials to provide a larger polymeric particle (e.g. a polymeric nanoparticle) carrying the $CaO_2$ nanoparticles. In this embodiment of the invention, the $CaO_2$ nanoparticles may be coated with the pH-responsive coating or these may be uncoated. However, it is generally preferred that they will be provided with a pH-responsive coating as herein described. Such polymeric particles may further contain one or more of the active agents herein described, e.g. a photosensitiser, a sonosensitiser, a radiosensitiser, or an enzyme capable of catalysing the degradation of $H_2O_2$ to oxygen such as catalase. Alternatively, these polymeric particles may be linked to one or more of such active agents.

In another aspect the invention thus provides a polymeric (nano)particle having embedded therein $CaO_2$ nanoparticles which optionally are provided with a pH-responsive coating, wherein said polymeric (nano)particle further comprises and/or is linked to one or more of the following active agents: a photosensitiser, a sonosensitiser, a radiosensitiser, or an enzyme capable of catalysing the degradation of $H_2O_2$ to oxygen, e.g. catalase.

The polymeric matrix in which the $CaO_2$ nanoparticles may be embedded may comprise any physiologically acceptable, biodegradable polymer. This may, for example, comprise poly(D,L-lactide-co-glycolide) (PLGA). The resulting polymeric particles may have at least one dimension (e.g. a diameter) in the range from 100 to 900 μm, preferably from 200 to 300 μm. As discussed above, these particles may also contain further components, including sensitisers (for example photosensitisers, sonosensitisers or radiosensitisers). In a further embodiment, these may also contain an enzyme capable of catalysing the degradation of hydrogen peroxide to oxygen, e.g. catalase.

Polymeric particles having $CaO_2$ nanoparticles embedded therein may be prepared using methods known in the art. For example, coated or uncoated $CaO_2$ nanoparticles (such as those are prepared as described in Examples 1 and 3) may be incorporated into larger polymeric nanoparticle platforms such as that described in Nomikou et al. (Acta Biomaterialia 44: 414-421, 2017). The nanoparticles may, for example, be suspended in acetone and/or dichloromethane containing PLGA (75:25; molecular weight: 66,000-107,000; Sigma Aldrich, UK). The PLGA polymer solution may also contain dissolved or suspended active entities such as sensitisers (e.g. photosensitisers, sonosensitisers or radiosensitisers) and/or imaging agents as described in this earlier reference prior to addition of the $CaO_2$ nanoparticles. The polymer suspension may then be dispensed slowly (e.g. over 7 to 15 mins) to a vigorously-stirred 1% (w/v) solution of polyvinyl alcohol (PVA, MW 30,000-70,000; 87-90% hydrolyzed; Sigma Aldrich, UK). Dispersion may be enhanced by exposure of the PVA solution to low frequency ultrasound during addition of the PLGA to the PVA solution, e.g. by exposure to a 6 mm ultrasound probe (Vibra-Cell; Sonics and Materials, Newton, Conn., USA) delivering ultrasound at a frequency of 20 kHz operated at 91 W (70% of net power output). Following dispersion, the suspension of PLGA nanoparticles containing the embedded $CaO_2$ nanoparticles may be cured by allowing the solvent (acetone or dichloromethane) to evaporate at normal pressure and room temperature, or under reduced pressure in a rotary evaporator. The particles may then be washed by filtration or centrifugation using ethanol or an aqueous solution at elevated pH (e.g. pH>8.5). The resulting particles may range in size from 100 to 900 μm and may be stored in the washing solution or, preferably, lyophilised.

Any of the particles herein described may be further functionalised to carry one or more of the following active agents: a photosensitiser, a sonosensitiser, a radiosensitiser, or an enzyme capable of catalysing the degradation of hydrogen peroxide to oxygen, e.g. catalase.

In one embodiment, the particles may be functionalised to carry an enzyme which is capable of catalysing the degradation of hydrogen peroxide to oxygen. One example of such an enzyme is catalase, although others may also be used. Catalase catalyses the decomposition of hydrogen peroxide to produce oxygen and so may serve to accelerate the production of oxygen at the target site. The presence of catalase also acts to control the levels of hydrogen peroxide generated on decomposition of the calcium peroxide and may, for example, ensure that such levels do not become too high in vivo.

The active agents may be incorporated into the particles in various ways, for example these may be linked to the pH-responsive coating which is provided on the $CaO_2$ nanoparticles, or these may be linked to the polymeric (nano)particle in which these are embedded. Alternatively, these may be embedded within the polymeric particle.

In one embodiment, the $CaO_2$ nanoparticles coated with the pH-responsive polymer may be linked to one or more of the active agents mentioned herein through covalent or non-covalent linkage, e.g. via electrostatic interaction, van der Waals forces and/or hydrogen bonding. Typically, these may be covalently bound by one or more covalent bonds. The following examples are illustrative of the type of methods which may be used to link the active agents to the pH-responsive coating of the nanoparticles:

In the case where the active agent is catalase: a monomeric component of the polymeric coating material may either be pre-formed with catalyse linked to it or catalase may be conjugated to the final polymer post preparation. In one embodiment, the enzyme catalase may be attached to the pH-responsive polymer to facilitate rapid conversion of the liberated hydrogen peroxide into molecular oxygen. This attachment may occur prior to polymerisation, for example, by reaction of methacrylic acid or a derivative thereof with catalase using carbodiimide-based coupling. The resulting catalase functionalised methacrylate monomer may then be co-polymerised with the remaining monomers (e.g. methyl methacrylate, ethyl acrylate and 2-(dimethylamino) ethyl methacrylate). In an alternative embodiment, methacrylic acid or a derivative thereof may be co-polymerised with the other monomers (e.g. methyl methacrylate, ethyl acrylate and 2-(dimethylamino) ethyl methacrylate), followed by grafting of the catalase onto the free carboxylic acid groups using carbodiimide-based chemistry.

In the case where the active agent is a photosensitiser and/or sonosensitiser, such as Rose Bengal (RB): attachment may occur before polymerisation, for example by reaction of methacrylic acid or a derivative thereof with amine-functionalised RB using carbodiimide-based coupling. The resulting RB-functionalised methacrylate monomer may then be co-polymerised with the other monomers (e.g. methyl methacrylate, ethyl acrylate and 2-(dimethylamino) ethyl methacrylate). Alternatively, methacrylic acid or a derivative thereof may be co-polymerised with the other monomers (e.g. methyl methacrylate, ethyl acrylate and 2-(dimethylamino) ethyl methacrylate) and amine-functionalised RB grafted onto the free carboxylic acid groups using carbodiimide-based chemistry. This methodology may be used for any of the other sensitisers (e.g. photosensitisers or sonosensitisers) listed herein.

In the case where the active agent is a drug which improves the sensitivity of the cells or tissues to radiotherapy (i.e. a radiosensitiser), such as 5-fluorouracil: attachment may occur before polymerisation, e.g. when methacrylic acid or a derivative thereof is reacted with 5-fluorouracil using carbodiimide-based coupling. The resulting 5-fluorouracil functionalised methacrylate monomer may then be co-polymerised with the other monomers (e.g. methyl methacrylate, ethyl acrylate and 2-(dimethylamino) ethyl methacrylate). Alternatively, methacrylic acid or a derivative thereof may be co-polymerised with the other monomers (e.g. methyl methacrylate, ethyl acrylate and 2-(dimethylamino) ethyl methacrylate) and 5-fluorouracil then grafted onto the free carboxylic acid groups using carbodiimide-based chemistry. Other suitable radiosensitisers may also be used such as gemcitabine.

The coated $CaO_2$ nanoparticles herein described may be used in conjunction with any known method of PDT or SDT which employs a photosensitiser or sonosensitiser. For use in such methods, the coated $CaO_2$ nanoparticles may be administered in combination with at least one photosensitiser (or precursor thereof) and/or at least one sonosensitiser. Depending on factors such as the condition to be treated, the mode of administration, etc., the coated nanoparticles may be co-administered with the active photosensitising or sonosensitising agent, for example in a single composition, or they may be administered sequentially or separately. More typically, these will be administered sequentially.

In another embodiment the coated $CaO_2$ nanoparticles herein described may be used in conjunction with any known method of radiotherapy. The method of radiotherapy may also involve co-administration of a radiosensitiser, however, it need not.

In a further aspect the invention thus provides a pharmaceutical composition comprising $CaO_2$ nanoparticles having a pH-responsive coating, together with a photosensitiser, a sonosensitiser, or a radiosensitiser, and, optionally, at least one pharmaceutical carrier or excipient.

In another aspect the invention relates to a product comprising (i) $CaO_2$ nanoparticles having a pH-responsive coating, and (ii) a photosensitiser, a sonosensitiser, or a radiosensitiser, for simultaneous or sequential use in a method of photodynamic therapy, sonodynamic therapy, or radiotherapy.

In a yet further aspect the invention relates to a kit comprising the following components: (i) $CaO_2$ nanoparticles having a pH-responsive coating, (ii) a photosensitiser, a sonosensitiser, or a radiosensitiser; and optionally (iii) instructions for the use of said components in a method of photodynamic therapy, sonodynamic therapy, or radiotherapy.

In an alternative embodiment, the photosensitising or sonosensitising agent may be directly attached to the coated $CaO_2$ nanoparticles as herein described. This may, for example, be achieved by attachment to the pH-responsive polymer coating which surrounds the particles.

Any known photosensitiser (or photosensitiser precursor) suitable for use in PDT may be employed in the invention. Examples of suitable photosensitisers and precursors thereof include the following: phthalocyanines such as aluminium phthalocyanines which optionally may be sulphonated (i.e. AlPcS), e.g. di-sulphonated aluminium phthalocyanines such as $AlPcS_2$ or $AlPcS_{2a}$, or aluminium phthalocyanine tetra-sulfonate ($AlPcS_4$); sulphonated tetraphenylporphyrins (e.g. $TPPS_{2a}$, $TPPS_4$, $TPPS_1$ and $TPPS_{2o}$); chlorins such as tetra(m-hydroxyphenyl)chlorins (m-THPC) (e.g. temoporfin which is marketed under the tradename Foscan); chlorin derivatives including bacteriochlorins and ketochlorins; mono-L-aspartyl chlorin e6 (NPe6) or chlorin e6; porphyrins including hematoporphyrin and benzoporphyrins; protoporphyrin IX (PpIX); 5-aminolevulinic acid (5-ALA) and derivatives of 5-ALA (leading to production of protoporphyrin IX).

Pharmaceutically acceptable salts of any of these photosensitisers (or precursors) may also be used. Such salts include salts with pharmaceutically acceptable organic or inorganic acids or bases.

Sonosensitisers are generally known in the art and any may be used in the invention. Sonosensitisers for use in the invention include any compounds capable of converting acoustic energy (e.g. ultrasound) into ROS that result in cell toxicity. It is well known that many known sonosensitisers can facilitate photodynamic activation and can also be used to render cells or tissues hypersensitive to light.

Examples of compounds suitable for use as sonosensitisers in the invention include phenothiazine dyes (e.g. methylene blue, toluidine blue), Rose Bengal, porphyrins (e.g. Photofrin®), chlorins, benzochlorins, phthalocyanines, napthalocyanines, porphycenes, cyanines (e.g. Merocyanine 540 and indocyanine green), azodipyromethines (e.g. BODIPY and halogenated derivatives thereof), acridine dyes, purpurins, pheophorbides, verdins, psoralens, hematoporphyrins, protoporphyrins and curcumins. Any known analogues or derivatives of these agents may also be used. Suitable derivatives include the pharmaceutically acceptable salts. Analogues include, for example, structural analogues of the cyanine-based dyes, such as the structural analogues of ICG and their pharmaceutically acceptable salts. Examples of these include the cyanine dyes IR820 and IR783, both of which are commercially available.

Preferred for use as sonosensitisers in the invention are methylene blue, Rose Bengal, indocyanine green (ICG, also known as Cardio Green), and any analogues and derivatives thereof.

In one embodiment the sonosensitiser for use in the invention may be conjugated (e.g. covalently or electrostatically) to a gas-filled microbubble as described, for example, in WO 2012/143739 and in McEwan et al., J. Control. Release 203: 51-6, 2015, the entire contents of which are incorporated herein by reference. Such microbubble-sonosensitiser "complexes" permit effective delivery of the sonosensitiser in a site-specific manner by a controlled destruction of the bubble using ultrasound. Subsequent or simultaneous sono-activation of the targeted sonosensitiser results in cell destruction at the target site and regression of tumor tissues. The use of a microbubble also leads to a reduction in toxic side-effects due to the shielding of the sonosensitiser from potential light activation prior to reaching the desired target site.

Microbubbles typically have a diameter of less than about 200 µm, preferably in the range from about 0.5 to about 100 µm. Particularly suitable are microbubbles having a diameter of less than about 10 µm, more preferably 1 to 8 µm, particularly preferably up to 5 µm, e.g. about 2 µm. The shell of the microbubble may vary in thickness and will typically range from about 10 to about 200 nm. Typically, the shell of the microbubble will comprise a surfactant (e.g. a lipid such as a phospholipid) or a polymer (e.g. a protein such as albumin, or another biocompatible polymer such as poly (vinyl alcohol), poly(D,L-lactide-co-glycolide), cyanoacrylate, poloxamers (Pluronics), polyethylene glycol, or polyvinylpyrrolidone. The microbubble shell may be further functionalised to incorporate therein or have bound thereto a ligand or targeting agent which is able to bind to a target cell or tissue. Examples of suitable targeting agents include antibodies and antibody fragments, cell adhesion molecules and their receptors, cytokines, growth factors and receptor ligands.

The gas within the core of the microbubble should be biocompatible and may be selected from air, nitrogen, oxygen, carbon dioxide, hydrogen; inert gases such as helium, argon, xenon or krypton; sulphur fluorides such as sulphur hexafluoride, disulphur decafluoride; low molecular weight hydrocarbons such as alkanes (e.g. methane, ethane, propane, butane), cycloalkanes (e.g. cyclopropane, cyclobutane, cyclopentane), alkenes (e.g. ethylene, propene); and alkynes (e.g. acetylene or propyne); ethers; esters; halogenated low molecular weight hydrocarbons (e.g. perfluorocarbons); and mixtures thereof.

Radiosensitisers are generally known in the art and any may be used in the invention. Radiosensitisers for use in the invention include any compounds that render tumour cells or tissues more sensitive to radiation therapy. Examples of radiosensitisers include the fluoropyrimidines, gemcitabine, and platinum analogues (e.g. cisplatin).

The compositions and methods herein described are suitable for the treatment of hypoxic cells or tissues within the body which are responsive to photodynamic and/or sonodynamic therapy, or to radiotherapy. These include malignant and pre-malignant cancer conditions, such as cancerous growths or tumours, and their metastases; tumours such as sarcomas and carcinomas, in particular solid tumours. The invention is particularly suitable for the treatment of hypoxic tumours.

Examples of tumours that may be treated using the invention are sarcomas, including osteogenic and soft tissue sarcomas; carcinomas, e.g. breast, lung, cerebral, bladder, thyroid, prostate, colon, rectum, pancreas, stomach, liver, uterine, hepatic, renal, prostate, cervical and ovarian carcinomas; lymphomas, including Hodgkin and non-Hodgkin lymphomas; neuroblastoma, melanoma, myeloma, Wilm's tumour; leukemias, including acute lymphoblastic leukaemia and acute myeloblastic leukaemia; astrocytomas, gliomas and retinoblastomas. Treatment of pancreatic cancer forms a preferred aspect of the invention.

The methods herein described may further be exploited ex vivo. For example, in autologous bone marrow transplantation in the treatment of leukaemia, bone marrow from the patient may be treated ex vivo to destroy cancerous cells. Once treated the bone marrow may then be used to re-establish haematopoiesis in the patient following radiation treatment. Alternatively, the methods of the invention may be carried out ex vivo to remove unwanted tissues from organs harvested for conventional transplant. Surgically removed tissues may be targeted and lesions destroyed prior to re-transplantation of the treated tissue.

For use in any of the methods herein described, the $CaO_2$ nanoparticles will generally be provided in a pharmaceutical composition together with at least one pharmaceutically acceptable carrier or excipient. This composition may further contain the selected photosensitiser (or precursor), sonosensitiser, or radiosensitiser. However, it is envisaged that in most cases the photosensitiser (or its precursor), the sonosensitiser, and radiosensitiser (when used) will be provided in a different formulation for separate administration to the patient. Administration of the composition containing $CaO_2$ nanoparticles prior to light, ultrasound or ionising radiation exposure enables the generation of oxygen at the target site prior to the main PDT, SDT or radiotherapy procedure. Typically, any sensitiser may be administered first, followed by the $CaO_2$ nanoparticles, and then followed up with light, ultrasound or radiation treatment.

The precise timing of administration of the composition containing $CaO_2$ nanoparticles, the photosensitising or sonosensitising agent, or the radiosensitiser (when used), and timing of irradiation or ultrasound to achieve the desired effects needs to take into account various factors including the nature (size, shape, etc.) of the nanoparticles, the cells to be treated and the quantity of nanoparticles taken up by the cells (which, in turn, will depend on the efficacy of the EPR for that particular tumour), the nature of the active molecules, the environment of the cells, and whether administration is direct to the target tissue or at a distal site, etc. Taking these considerations into account appropriate timings may readily be determined by those skilled in the art. In one embodiment, $pO_2$ at the target site may be monitored and when it reaches a maximum (or a certain threshold), light, ultrasound or radiation treatment may be initiated. As noted above, the sensitiser will generally be given to the patient prior to the $CaO_2$ nanoparticles.

The pharmaceutical compositions for use according to the invention may be formulated using techniques well known in the art. The route of administration will depend on the intended use. Typically, these will be administered systemically and may thus be provided in a form adapted for parenteral administration, e.g. by intradermal, subcutaneous, intraperitoneal or intravenous injection. Alternatively, these may be administered via intra or peri-tumoral injection. Suitable pharmaceutical forms include suspensions and solutions which contain the $CaO_2$ nanoparticles together with one or more inert carriers or excipients. Suitable carriers include saline, sterile water, phosphate buffered saline and mixtures thereof.

The compositions may additionally include other agents such as emulsifiers, suspending agents, dispersing agents, solubilisers, stabilisers, buffering agents, preserving agents, etc. The compositions may be sterilised by conventional sterilisation techniques.

Solutions containing the $CaO_2$ nanoparticles may be stabilised, for example by the addition of agents such as viscosity modifiers, emulsifiers, solubilising agents, pH adjusters, etc. When using any pH-adjusters, these may be used to stabilise the solutions at high pH. Prior to use (e.g. at the point of injection) these may be adjusted down in pH to a range suitable for physiological use.

Preferably, the $CaO_2$ nanoparticle compositions for use in the invention will be used in the form of an aqueous suspension of the $CaO_2$ nanoparticles in water, saline or a buffered saline solution, e.g. phosphate-buffered saline.

PDT methods are generally known in the art and involve administration to the affected cells or tissues of a photosensitiser or precursor of a photosensitiser followed by exposure of said cells or tissues to light (i.e. irradiation) to achieve the desired photoactivation and generation of cytotoxic species. The period of time between administration of the photosensitiser (or precursor) and exposure to light (i.e. the incubation time) will depend on the nature of the active compound, the nature of the composition in which it is presented, the particular condition to the treated, and the mode of administration. Generally, it is necessary that the photosensitiser (or precursor) has been taken up by the cells of the tissue to be treated, if necessary converted into an active photosensitiser, and achieved an effective tissue concentration at the intended target site prior to photoactivation. Typically, the incubation time will be up to 10 hours, for example about 30 minutes to 6 hours, or 1 hour to 4 hours. Direct local administration of the active compound may result in shorter incubation times, for example, from about 1 minute to about 3 hours, e.g. 5 minutes to about 2 hours. In cases where the active photosensitiser is administered orally or sublingually and systemic uptake is required, incubation times will generally be longer, e.g. up to 6 hours, e.g. 2 to 5 hours or 3 to 4 hours. Suitable incubation times required to maximise the concentration of the photosensitiser at the target site and minimise its concentration in surrounding tissues may readily be determined by those skilled in the art.

After administration of the photosensitiser (or precursor) to the target site it is exposed to light to achieve the desired photoactivation and PDT treatment. The precise timing for irradiation and choice of light intensity (i.e. fluence rate) may readily be selected by those skilled in the art taking into account factors such as the nature of the photosensitiser, target location/depth and skin colour. Additionally, administration of the photosensitiser dose may be fractionated in order to optimise sensitisation. A light intensity reaching the target tissue may be in the range of 0.5 to 200 $mW/cm^2$, e.g. about 100 $mW/cm^2$. Suitable sources of light include lamps and lasers, e.g. LED lamps. For irradiation of internal surfaces of the body, optical fibres connected to an external light source may be used. For some uses, various devices such as catheters may be required for light delivery to areas of interest. Generally, the length of time for the irradiation step will be of the order of minutes to several hours, e.g. preferably up to 60 minutes e.g. from 1 to 30 minutes, e.g. from 0.5 to 3 minutes or from 1 to 5 minutes.

Suitable dose levels of light may be determined by those skilled in the art but may, for example, range from about 10 to about 200 $Joules/cm^2$. The wavelength of light used for irradiation should be selected based on the choice of photosensitiser in order to provide an efficacious PDT effect. Light having wavelengths of between 300-800 nm may be appropriate. Red light (600-670 nm) is particularly preferred since light at this wavelength penetrates more deeply into tissues. A single irradiation may be used or alternatively the light may be delivered in a number of fractions, e.g. a few to several minutes between irradiations. The irradiation time is dependent on factors such as the fluence rate and the desired light dose and can be determined by those skilled in the art.

SDT methods for use in the invention involve the administration of a therapeutically effective amount of a composition containing the sonosensitiser. Following distribution to the desired target area of the body, the target area is exposed to ultrasound at a frequency and intensity to achieve the desired therapeutic effect. The effective dose of the composition will depend on the nature of the sonosensitiser, the mode of administration, the condition to be treated, the patient, etc. and may be adjusted accordingly.

The frequency and intensity of the ultrasound which may be used can be selected based on the need to achieve sonoactivation of the sonosensitser. Ultrasound frequencies will typically be in the range 20 kHz to 10 MHz, preferably 0.1 to 2 MHz. Ultrasound may be delivered as either a single frequency or a combination of different frequencies. Intensity (i.e. power density) of the ultrasound may range from about 0.1 $W/cm^2$ to about 1 $kW/cm^2$, preferably from about 1 to about 50 $W/cm^2$. Treatment times will typically be in the range of 1 ms to 20 minutes and this will be dependent on the intensity chosen, i.e. for a low ultrasound intensity the treatment time will be prolonged and for a higher ultrasound intensity the treatment time will be lower. Ultrasound may be applied in continuous or pulsed mode and may be either focused or delivered as a columnar beam. Ultrasound may also be provided at multiple frequencies, either simultaneously or sequentially, e.g. 20 kHz together with 1 MHz or 20 kHz followed by 1 MHz, respectively. Alternatively, ultrasound may be delivered in a modulated mode with respect to frequency and/or amplitude.

Any radiation source capable of producing acoustic energy (e.g. ultrasound) may be used in the methods herein described. The source should be capable of directing the energy to the target site and may include, for example, a probe or device capable of directing energy to the target tissue from the surface of the body.

In the case where the sonosensitiser used is one which also responds to light, ultrasound activation may be accompanied by light activation.

Radiotherapy methods are generally known in the art and involve exposure of target cells or tissues to ionising radiation to achieve DNA damage and the resulting cytotoxic effect. Often, radiotherapy is combined with chemotherapy (which involves the combined use of a "radiosensitiser") that makes the target cells or tissue more sensitive to radiation treatment. The period of time between administration of the radiosensitiser and exposure to radiation (i.e. the incubation time) will depend on the nature of the active compound, the nature of the composition in which it is presented, the particular condition to the treated, and the mode of administration. Generally, it is necessary that the radiosensitiser has been taken up by the cells of the tissue to be treated and achieved an effective tissue concentration at the intended target site prior to radiation treatment. Typically, the incubation time will be up to 1 hour, for example about 30 minutes to 6 hours, or 1 hour to 4 hours. In cases where the radiosensitiser is administered orally or sublingually and systemic uptake is required, incubation times will generally be longer, e.g. up to 6 hours, e.g. 2 to 5 hours or 3 to 4 hours. Suitable incubation times required to maximise the concentration of the radiosensitiser at the target site and minimise its concentration in surrounding tissues may readily be determined by those skilled in the art.

During radiotherapy, and optionally after administration of any radiosensitiser, the target site may then be exposed to external beam radiation (EBR) to achieve the desired radiotherapy treatment. The precise timing for irradiation and choice of intensity (i.e. radiation dose) may readily be selected by those skilled in the art taking into account factors such as the nature of any radiosensitiser which is used, target location/depth and stage of the disease. Additionally, administration of the radiation dose may be fractionated in order to optimise its effect. The total radiation dose reaching the target tissue may be in the range of 10 to 60 Gy. Commonly, the total radiation dose may be administered in fractions over the course of several weeks, e.g. 40 Gy in 25 fractions over 5 weeks. Suitable sources of radiation include linear accelerators (linacs). Generally, the length of time for the irradiation step will be of the order of minutes, preferably up to 30 minutes, e.g. from 10 to 30 minutes.

Alternatively, radiation may be provided by a brachytherapy-based method or using targeted radionuclide therapy.

The invention will now be described further with reference to the following non-limiting Examples and the accompanying figures in which.

Figure 7:
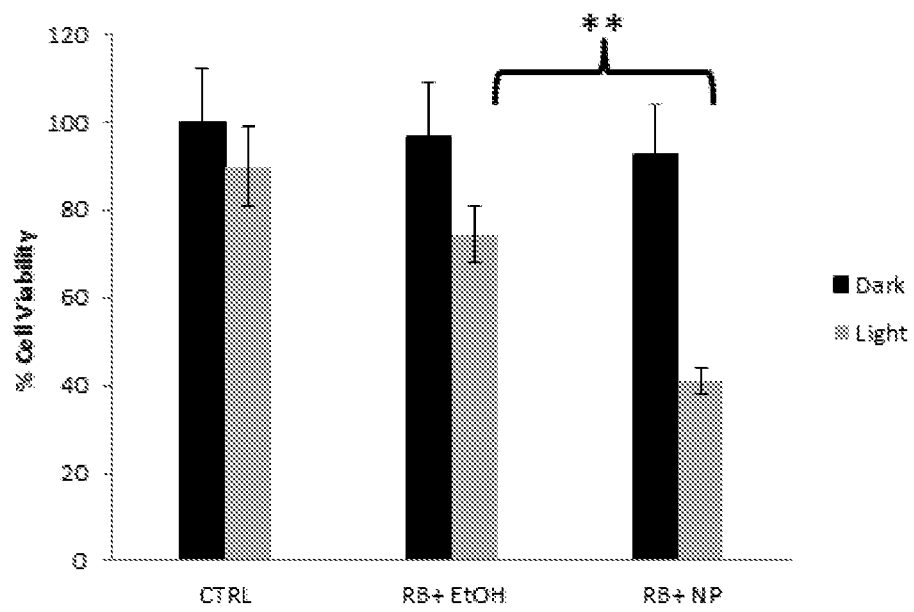
Figure 8:
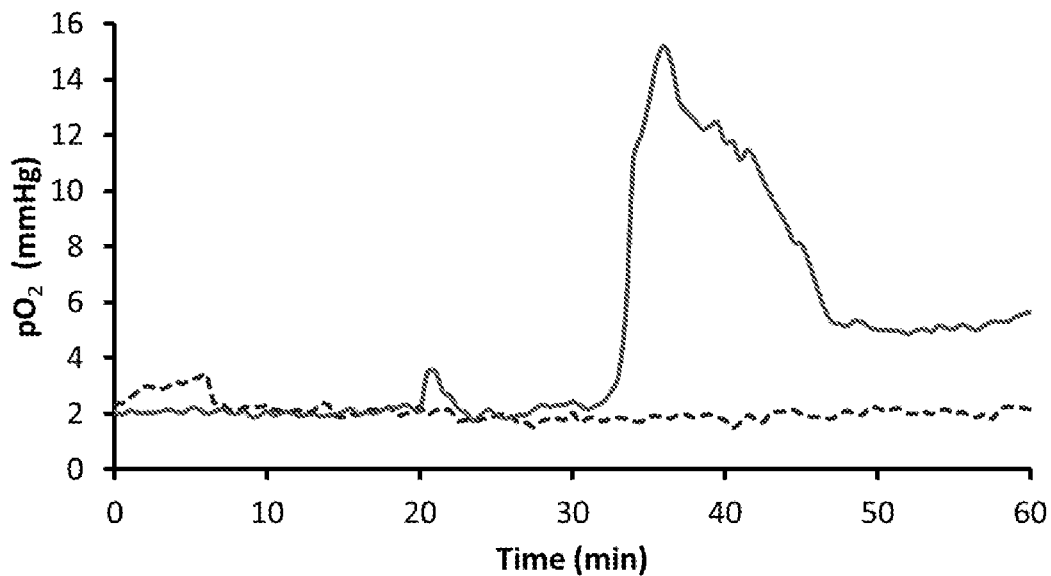
Figure 8:
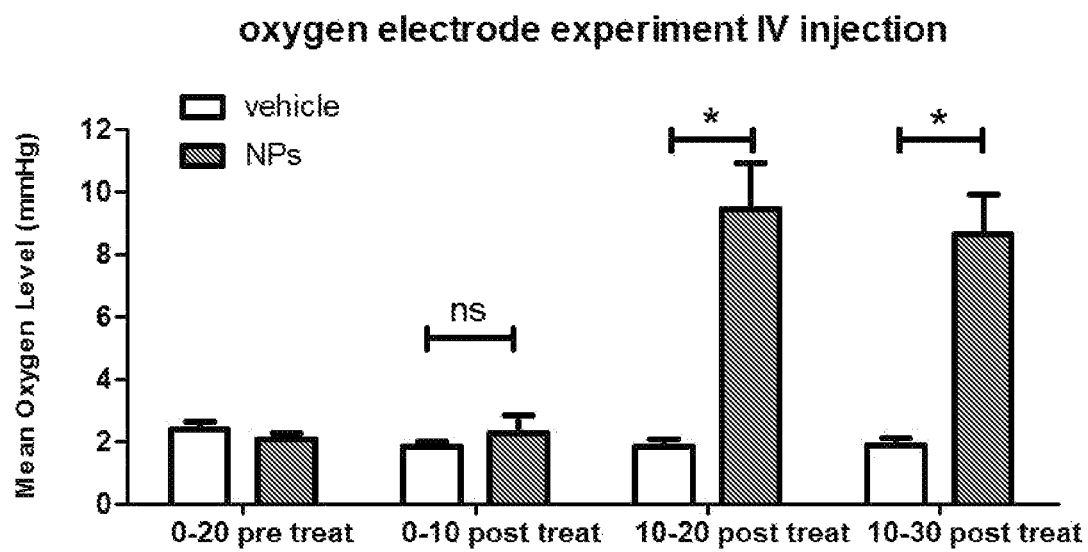
Figure 9:
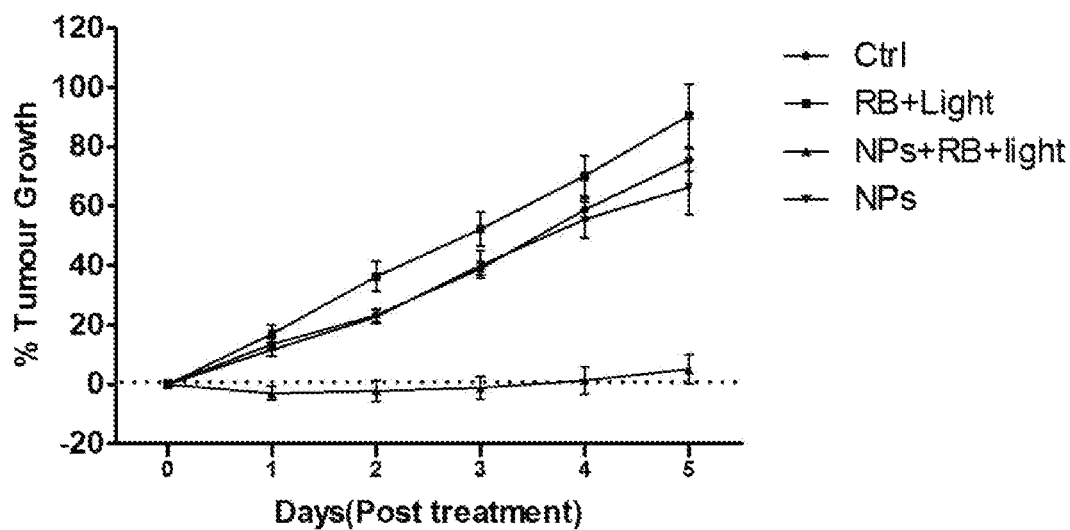
Figure 9:
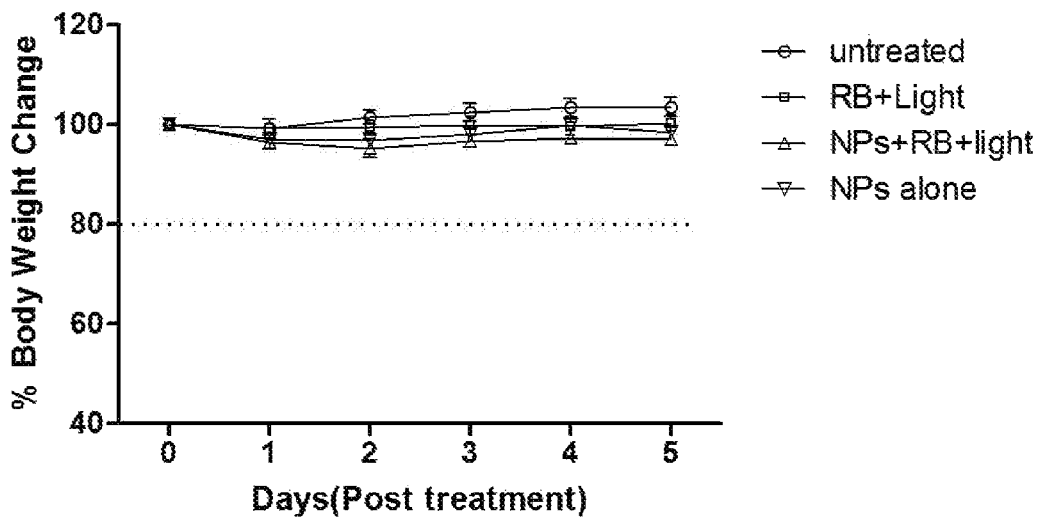

FIG. 7 is a plot of cell viability for BxPC-3 cells, cultured under hypoxic conditions with (i) no treatment (CTRL dark bar) or after treatment with (ii) light only (CTRL light bar) (iii) RB only in an EtOH vehicle (RB+EtOH black bar) (iv) RB in an EtOH vehicle+light (RB+EtOH light bar) (iv) RB+$CaO_2$ NP in an EtOH vehicle (RB+NP dark bar) (vi) RB+$CaO_2$ NP+ light in an EtOH vehicle (RB+NP dark bar);

FIG. 8 shows: (a) Plot of average tumour $pO_2$ in mice bearing ectopic MiaPaca-2 pancreatic tumours recorded for 20 min before and 40 min following an IV injection of polymer coated $CaO_2$ NPs in a PBS (pH 7.4±0.1) vehicle (unbroken line) or vehicle only (dashed line) (injection occurred at t=20 mins); and (b) Plot showing the mean tumour $pO_2$ for various time intervals before and following IV administration of polymer coated $CaO_2$ NPs, obtained from integration of the plot shown in (a). n=3, *$p \leq 0.05$;

FIG. 9 shows: (a) Plot of % change in tumour volume against time for SCID mice bearing human xenograft Mia-PaCa2 pancreatic tumours treated with (i) no treatment (squares) (ii) PDT only (circles) (iii) polymer coated $CaO_2$ NPs only (diamonds) and (iv) polymer coated $CaO_2$ NPs and PDT (triangles); and (b) Plot of average body weight for each group of mice over the time course of the experiment. ***$p \leq 0.01$.

EXAMPLES

Reagents and Equipment:

Calcium chloride, PEG 200, 1M ammonia solution, 35% hydrogen peroxide, sodium hydroxide, phosphate buffered saline (PBS), luminol, methanol, ethanol, hexane, chloroform, Rose Bengal, singlet oxygen sensor green (SOSG), anhydrous tetrahydrofuran (THF), 2-(dimethylamino)ethyl methacrylate, methyl methacrylate, ethyl acrylate and 1,1'-Azobis(cyclohexanecarbonitrile) (ABCN) were purchased from commercial sources at the highest possible grade. BxPC-3 and MiaPaCa cells were obtained from the American Type Culture Collection (ATCC) and matrigel from BD Biosciences, Erembodegem, Belgium. SCID mice (C.B-17/IcrHanHsd-PrkdcSCID) were bred in house. Scanning electron microscopy (SEM) analysis was conducted using an "FEI Quanta" scanning electron microscope while dynamic light scattering (DLS) measurements were performed using a Malvern Zetasizer 3000HSA (Malvern, Worcs., UK). Dissolved oxygen measurements were recorded using a Thermo Scientific™ DO Probe Orion™ 083005MD (Fisher Scientific, Ottawa, ON, Canada) while nanoparticle solutions were mixed using a Silverson homogenizer (Silverson Machines Ltd, Chesham, U.K.). Fluorescence measurements were undertaken using a Cary Eclipse spectrophotometer while 96 well plates were analysed using a Fluostar Omega plate reader. Tumour $pO_2$ measurements were performed using an Oxylite oxygen electrode sensor (Oxford Optronics, Oxford, UK). NMR spectra were obtained on Varian 500 MHz instrument at 25.0±1° C. and processed using Bruker software. Mass spectra were obtained using a Finnegan LCQ-MS instrument. Error in measurements was expressed as % standard error of the mean while statistical analysis was undertaken using 2-tailed Students t-test.

Example 1—Preparation of Uncoated $CaO_2$ NPs $CaO_2$ nanoparticles ($CaO_2$ NPs) were prepared following a hydrolysis-precipitation procedure similar to that developed by Khodaveiside et al. (Journal of hazardous materials, 192(3): 1437-1440, 2011). This utilised $CaCl_2$ as a calcium precursor and polyethylene glycol 200 (PEG200) as a surface modifier.

Ammonia solution (15.0 mL, 1M) and PEG 200 (120.0 mL, 0.6744 mol) was added to a stirred solution of calcium chloride (3.0 g, 0.027 mol) in distilled water (30 mL). A solution of 35% $H_2O_2$ (15 mL, 0.17 mol) was then added to the mixture at a rate of 3 drops per minute and the colourless solution stirred for a further 2 hours at room temperature. A NaOH solution (0.1 M) was then added until a pH value of 11.5 was achieved when the solution changed to a white coloured suspension. The precipitate was separated by centrifugation and the resulting pellet washed three times with NaOH (25 mL, 0.1 M). The powder was then washed with distilled water until the filtrate pH reached 8.4 and the powder dried in vacuo at 80° C. for 2 hours. The resulting particles were suspended in ethanol and sonicated for 5 minutes. The suspension was passed through a Millex Filter Unit (0.45 μm) to isolate larger particles and the filtrate concentrated to dryness affording the $CaO_2$ nanoparticles as a white powder. The size and size distribution of the nanoparticles was determined by SEM and DLS.

Figure 1:
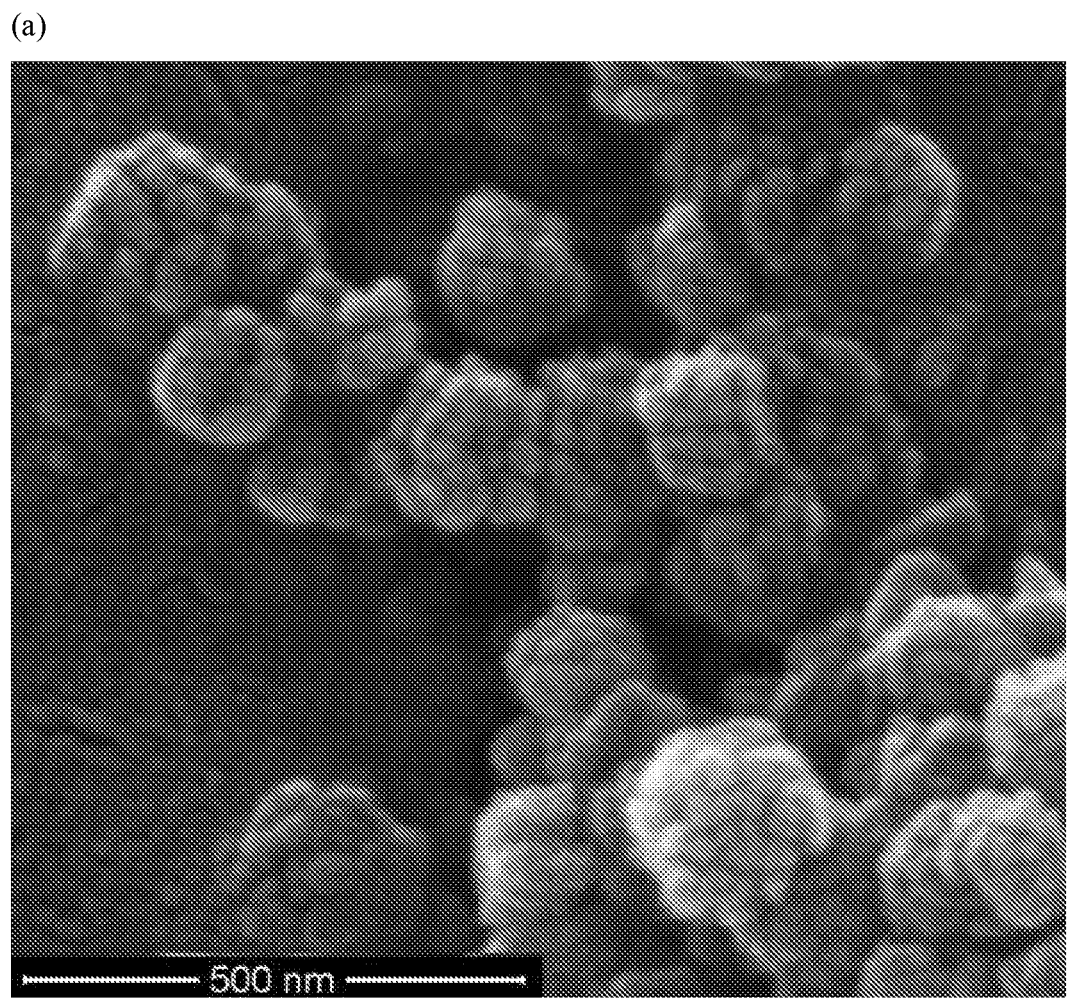
FIG. 1 shows a representative SEM image (a) and DLS plot (b) of $CaO_2$ NPs prepared in Example 1.
Figure 1:
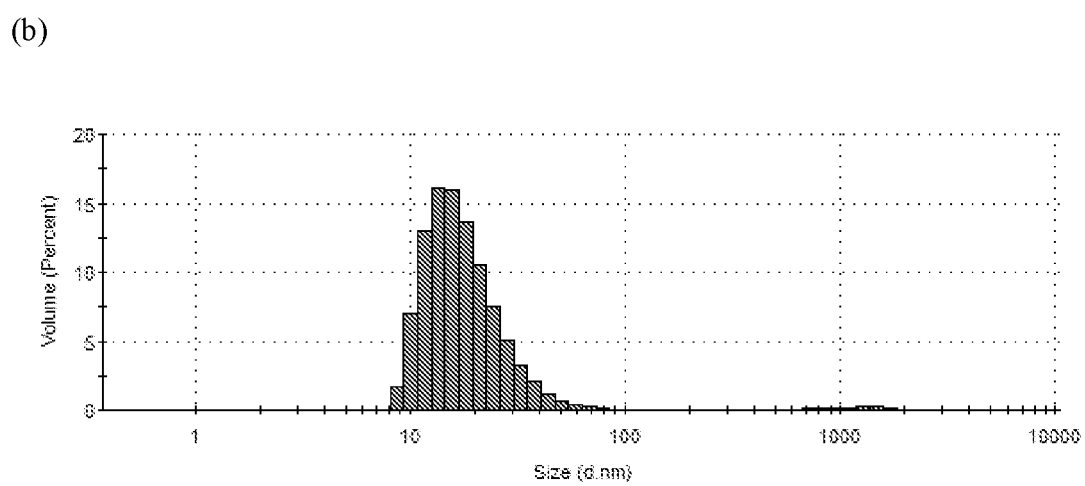

The resulting particles were analysed by SEM and found to be spherical in shape with an average diameter of 116.0±7.6 nm (FIG. 1a). Closer inspection of the particle morphology revealed the appearance of several smaller particles coalesced together to form the larger sized NPs. This was confirmed when an ethanol solution containing the NPs was analysed using DLS where the particle diameter was found to be much smaller at 21.0 nm±11 nm (FIG. 1b).

Example 2—Determination of $CaO_2$ Content in the Uncoated $CaO_2$ NPs

The amount of active $CaO_2$ contained within the NP powder produced in Example 1 was determined by measuring the luminescence generated when a fixed amount of the NP powder was dissolved in an aqueous luminol solution. The hydrogen peroxide generated from reaction of $CaO_2$ with the aqueous medium subsequently reacts quantitatively with luminol to produce a chemiluminescent signal that is proportional to the amount of hydrogen peroxide present.

The active $CaO_2$ content of the NPs was determined by reaction with luminol in PBS. A chemiluminescence intensity/concentration calibration curve for the reaction of $H_2O_2$ with luminol was performed according to the procedure adopted by Komagoe et al. (Analytical sciences, 22(2): 255-258, 2006). $CaO_2$ NPs in ethanol solution (50 μL, 35.6 μM) were added to a luminol solution (50 μL, 10 mg/mL) and the chemiluminescence intensity determined using a plate reader. The $CaO_2$ content was determined by indirectly measuring the number of moles of $H_2O_2$ produced (by reference to the calibration graph) from the fixed mass of $CaO_2$ powder and assuming all the available $CaO_2$ was converted to $H_2O_2$. Using this approach, the amount of active $CaO_2$ present in the NP powder was determined as 44.9±2.3% with the remaining mass due to excipients such as PEG.

Example 3—Coating of $CaO_2$ NPs with Polymer

Figure 2:
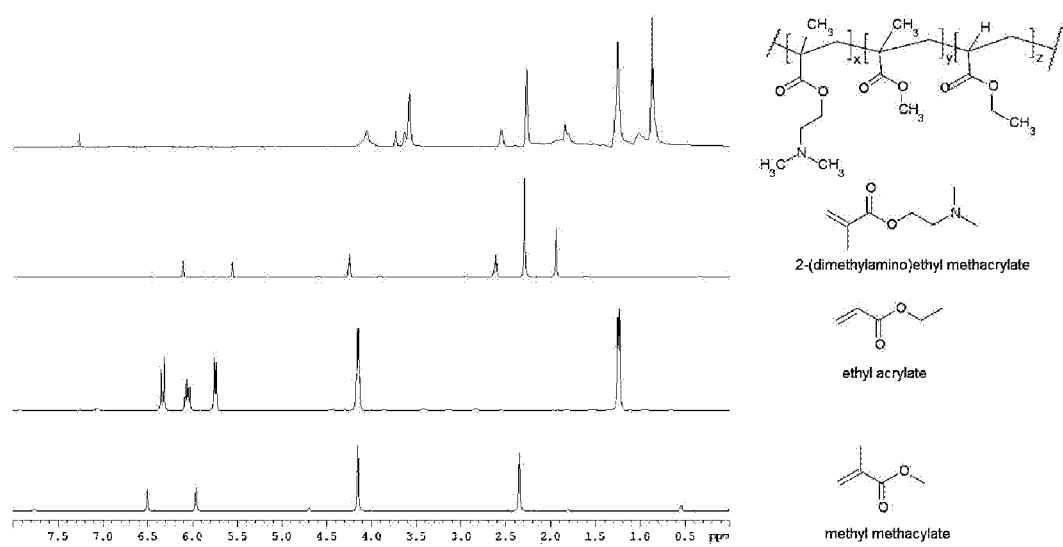
FIG. 2 shows stacked $^1H$ NMR spectra of (i) methyl methacrylate; (ii) ethyl acrylate; (iii) 2-(dimethylamino) ethyl methacrylate; and (iv) pH-responsive polymer 1 prepared in Example 3.

Polymer 1 was prepared by the free radical co-polymerisation of 2-(dimethylamino)ethyl methacrylate, methyl methacrylate and ethyl methacrylate in a 2:1:1 ratio. Polymer 1 contains a tertiary amine side chain making it possess low aqueous solubility as the free base but which becomes soluble once ionised. The successful preparation of polymer 1 was confirmed by $^1H$ NMR spectroscopy with the stacked spectra of each monomer and polymer 1 shown in FIG. 2. The olefinic protons present in the spectra of the monomers between 5.5 and 6.5 ppm were not present in polymer 1 indicating they had been successfully polymerised to form the backbone of polymer 1. In addition, the peaks were much broader in the spectrum of polymer 1 than in the monomers, which is characteristic of protons in or near the backbone of polymers due to an ineffective averaging of their chemical shift anisotropies.

Figure 3:
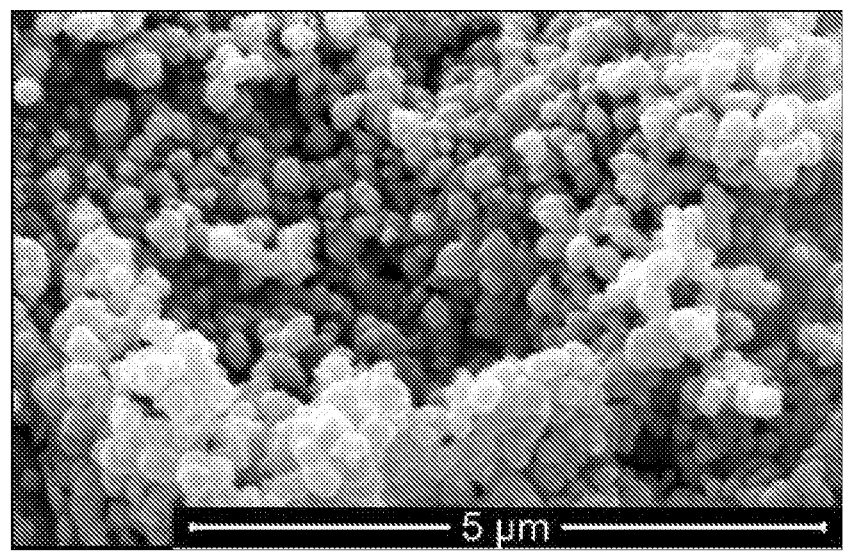
FIG. 3 shows a representative SEM image (a) and DLS plot (b) of polymer coated $CaO_2$ NPs prepared in Example 3.
Figure 3:
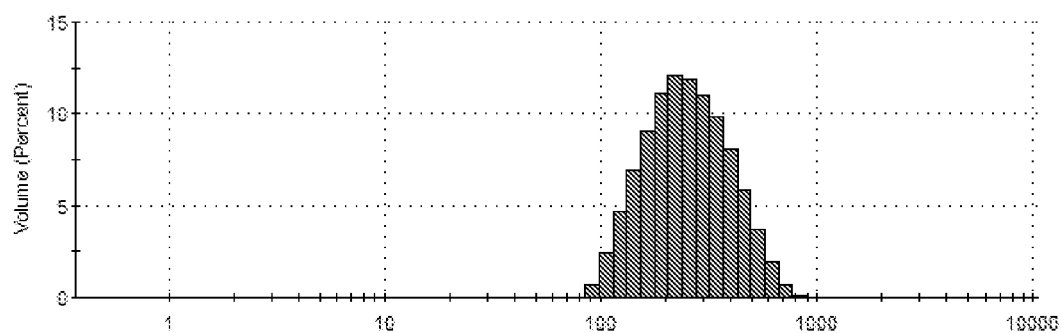

Polymer 1 was then used to coat the $CaO_2$ NPs produced in Example 1 using a modified oil-in-water emulsion technique. A SEM image of the resulting polymer coated $CaO_2$ NPs is shown in FIG. 3a and again reveals spherical particles with an average diameter of 248±17 nm which was similar to the hydrodynamic diameter (278±71 nm) determined by DLS (FIG. 3b).

Preparation of Polymer 1:
2-(dimethylamino)ethyl methacrylate (157.2 mg, 1 mmol), methyl methacrylate (100.1 mg, 2 mmol) and ethyl acrylate (100.1 mg, 1 mmol) and a catalytic amount of the free radical initiator (ABCN) were dissolved in anhydrous THF (5 mL) and placed in a Carious reaction vessel. The contents were then subjected to three freeze-pump-thaw cycles, sealed under vacuum and placed in a Carious oven at 80° C. for 72 hours. The contents were removed and hexane (20 mL) added to the facilitate precipitation followed by centrifugation for 5 min at 6000 rpm. The supernatant was removed, the pellet containing 1 re-dissolved in anhydrous THF and precipitated again with hexane a centrifuged at 6000 rpm. This purification procedure was repeated twice further before the pellet was dried in vacuo at 80° C. and characterised by $^1H$ NMR spectroscopy.

Coating of $CaO_2$ NPs with Polymer 1 to Form "1-$CaO_2$ NPs":
$CaO_2$ NPs were coated with polymer 1 using a modified single emulsion method (Choi et al., International journal of pharmaceutics, 311(1): 223-228, 2006). $CaO_2$ NPs (10 mg) were dispersed in hexane (10 mL) and sonicated for 5 min. The NP suspension was then added dropwise at a rate of 2 mL/min to a solution of polymer 1 (100 mg, 0.36 μmol) in ethanol (40 mL) using a Silverson homogeniser at 9000 RPM for 5 mins to ensure efficient mixing. After a further mixing period for 6 hours, the emulsion was freeze dried and reconstituted in sterile water when required for use. The 1-$CaO_2$ NPs were characterised using SEM and DLS.

Example 4—Dissolved Oxygen Experiments Using Uncoated and Coated $CaO_2$ NPs For the dissolved oxygen experiments involving the uncoated $CaO_2$ NPs, an ethanol solution containing the NPs (10.0 mg, 24 mmol) was added to 10 mL of de-oxygenated PBS solvent. The dissolved oxygen was then measured and recorded every 1 min using a dissolved oxygen meter. For dissolved oxygen experiments involving the 1-$CaO_2$ NPs, separate solutions of de-oxygenated water were pH adjusted to pH 7.4 or 6.2. The 1-$CaO_2$ NPs (2 mg) were then added to each solution and the dissolved oxygen was measured using a dissolved oxygen meter 3 min following addition. Results were compared against identical solutions in the absence of 1-$CaO_2$ NPs. Both sets of experiments were repeated in triplicate.

Figure 4:
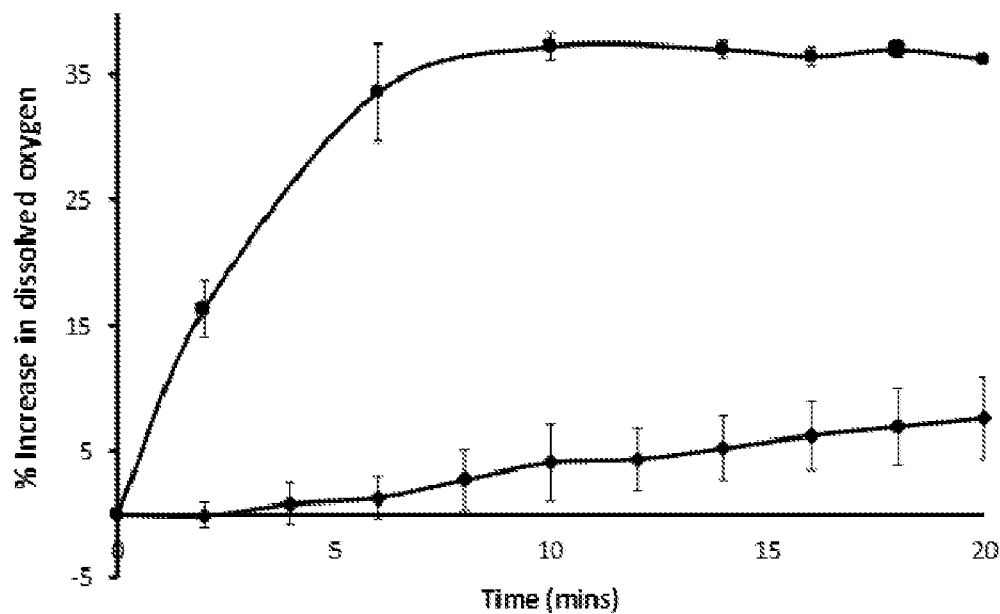
FIG. 4 is a plot of increase in dissolved oxygen for a solution of PBS against time over a period of 20 minutes in the absence (diamonds) or presence (circles) of uncoated $CaO_2$ NPs.

To determine the ability of the uncoated $CaO_2$ NPs to generate molecular oxygen upon contact with water and improve oxygen levels in the resulting solution, a simulated hypoxic environment was generated by de-oxygenating a solution of PBS (pH=7.4±0.1). A fixed amount of the $CaO_2$ NPs was added to the solution and the amount of dissolved oxygen present in the solution determined as a function of time. The results are shown in FIG. 4 and reveal a rapid increase in dissolved oxygen level (37.25%) 10 minutes after NP addition with no further increase observed over the next 16 min suggesting all the $CaO_2$ NPs were used up. In contrast, a degassed PBS solution that was exposed to the open atmosphere increased by only 4.10% over the same time period. These results demonstrate that the $CaO_2$ NPs rapidly decompose when they come into contact with aqueous medium generating a significant enhancement in the oxygen levels of the resulting solution.

Figure 5:
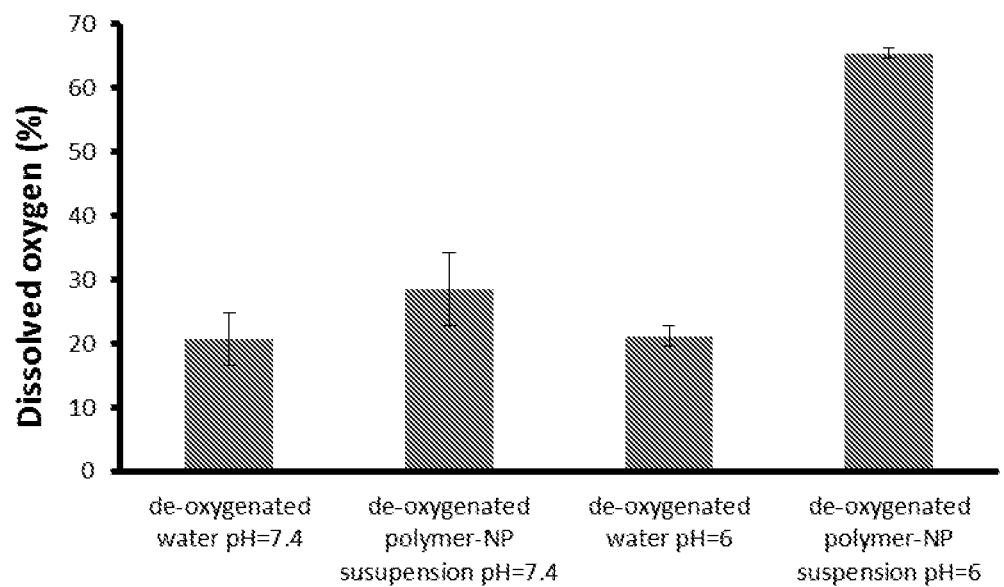
FIG. 5 is a plot of % dissolved oxygen for solutions of de-oxygenated PBS solution at pH 6.0 and pH 7.4 in the absence and presence of polymer coated $CaO_2$ NPs.

The ability of the 1-$CaO_2$ NPs to generate oxygen as a function of solution pH was determined by monitoring the increase in dissolved oxygen. De-oxygenated aqueous solutions containing 1-$CaO_2$ NPs (1 mg/mL) were pH adjusted to either pH 7.4 or pH 6.0 and the change in dissolved oxygen measured at each pH 5 minutes later. The results are shown in FIG. 5 and reveal a 45% increase in dissolved oxygen at pH 6.0 compared to only 7% increase at pH 7.4. This increase in dissolved oxygen results from dissolution of the polymer coating at lower pH that exposes the $CaO_2$ core to the aqueous environment.

The pH of an aqueous suspension containing 1-$CaO_2$ NPs (2 mg in 10 mL) was lowered from pH 7.4 to pH 6.2 in approximate 0.1 pH increments. The visual appearance of the resulting suspensions/solutions was photographed at pH 7.4, 6.9 and 6.2. As the pH was adjusted from pH 7.4 to pH 6.2, the visual appearance changed from a milky suspension to a more transparent solution. These results suggest that the 1-$CaO_2$ NPs should remain stable in the systemic circulation at pH=7.4 but become activated to release $O_2$ when in the more acidic tumour microenvironment.

Example 5—Determination of Singlet Oxygen Generation

The ability of the uncoated $CaO_2$ NPs to enhance PDT mediated singlet oxygen generation was determined using the singlet oxygen probe sensor green (SOSG). SOSG is inherently non-fluorescent but reacts with singlet oxygen to generate a fluorescent product with the fluorescence intensity being proportional to the amount of singlet oxygen generated (Faulkner et al., Free Radical Biology and Medicine, 15(4): 447-451, 1993).

Figure 6:
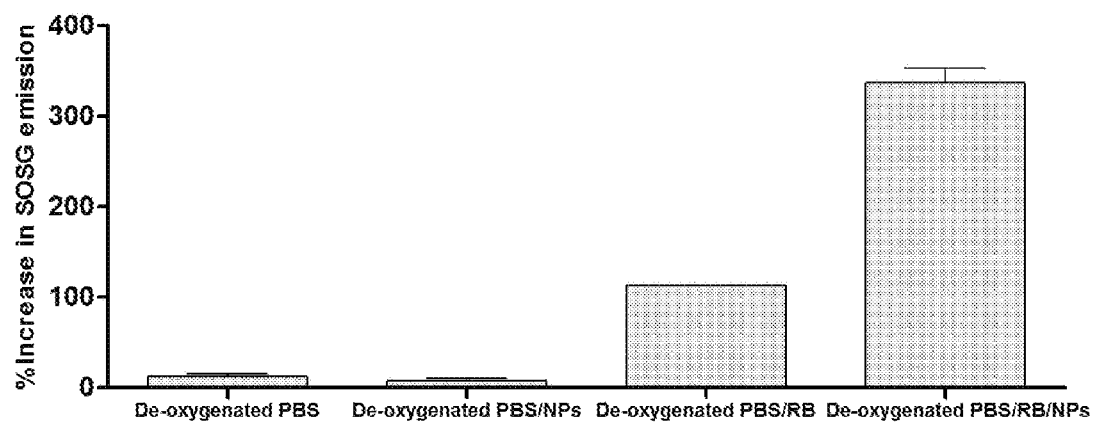
FIG. 6 is a plot of % increase in SOSG fluorescence at 510 nm for solutions containing (i) de-oxygenated PBS (ii) de-oxygenated PBS and $CaO_2$ NPs (35.6 µM) (iii) de-oxygenated PBS and 5 µM Rose Bengal (RB) and (iv) de-oxygenated PBS, 5 µM Rose Bengal and $CaO_2$ NPs (35.6 µM)

A de-oxygenated PBS solution (2:98; EtOH:$H_2O$) containing SOSG (2.5 µM) and the sensitiser Rose Bengal (5 µM) was prepared and an ethanol solution containing $CaO_2$ NPs (35.6 µM) added. Immediately, the solution was then irradiated with white light for 5 min at which point the fluorescence intensity at 530 nm was measured using a fluorescence spectrometer. Control experiments in the absence of the $CaO_2$ NPs (i.e. RB, SOSG and light) and $CaO_2$NPs only (i.e. $CaO_2$ NPs, SOSG, and light) were also conducted for comparative purposes. The results are shown in FIG. 6 and reveal a significant increase (324.8%, p<0.001) in the amount of SOSG fluorescence observed for the solution containing $CaO_2$ NPs, RB and treated with light compared to the control experiments, indicating the ability of the NPs to provide oxygen during the photodynamic event and enhance ROS generation in this simulated hypoxic environment.

Example 6—In Vitro PDT Experiments Using Uncoated $CaO_2$ NPs

Having determined the ability of the $CaO_2$ NPs to improve the light induced ROS generation of Rose Bengal in a simulated hypoxic environment, the next step was to determine if this improved ROS generation would also result in increased Rose Bengal mediated PDT killing of human BxPC-3 pancreatic cancer cells.

BxPc3 cells were seeded in a 96 well plate at a density of $5 \times 10^4$ cells per well. The cells were cultured in an anaerobic cabinet ($O_2/CO_2/N_2$, 0.1:5:94.9 v/v/v) for 3 hours to generate a hypoxic environment and then spiked with RB (1 µM) and incubated for a further 3 hours under anaerobic conditions. This concentration of RB is much lower than normally used in PDT cell-based studies (~5 µM) and was chosen to enable a moderate PDT effect in the absence of $CaO_2$ NPs so that any beneficial effect provided by the NPs could be determined (Chan et al., Tissue engineering, 13(1): 73-85, 2007). The cells were then incubated with an ethanol: PBS (50:50) solution of the NPs (50 µM) for 5 min before being exposed to light from a 532 nm emitting LED for 30 sec. The NP solution was then removed, the cells washed with fresh PBS and incubated in fresh media under normoxic conditions for a further 21 hours before cell viability was determined using a MTT assay. The use of a 50% ethanolic NP solution in these experiments was not ideal but care was taken to ensure that contact time with the cells was kept to a minimum. We also conducted vehicle only, RB only, light only and NP only controls for comparative purposes. The results are shown in FIG. 7 and reveal a significant (p<0.01) reduction in viability for those cells treated with PDT in the presence of $CaO_2$ NPs (33.3%) compared to PDT treatment alone (10.8%). In addition, there was no observable toxicity exhibited by the nanoparticles themselves at the concentration used in this experiment. These results suggest that treatment of hypoxic BxPC3 with $CaO_2$ NPs prior to PDT treatment can enhance oxygen levels improving the PDT mediated efficacy.

Example 7—Determination of the Effect of $CaO_2$ NPs on Tumour $pO_2$

To determine the ability of the 1-$CaO_2$ NPs to enhance tumour oxygenation in an in vivo model, ectopic human xenograft MiaPaca-2 tumours were established in SCID mice. The Mia-PaCa-2 model is known to form hypoxic tumours and has previously been used in efficacy experiments involving hypoxia activated prodrugs. Unlike the BxPC-3 cell line, MiaPaca-2 cells also express the KRAS mutation making it a more representative model of the disease in vivo.

Mia-Paca-2 cells were maintained in RPMI-1640 medium supplemented with 10% foetal calf serum. Cells were cultured at 37° C. under 5% $CO_2$ in air. The cells ($5 \times 10^6$) were re-suspended in 100 µL of Matrigel® (BD Biosciences, Erembodegem, Belgium) and implanted subcutaneously into the rear dorsum of male SCID mice. Animals were treated humanely and in accordance with licensed procedures under the UK Animals (Scientific Procedures) Act, 1986. Tumour formation occurred approximately 5 weeks after implantation and tumour measurements were taken every other day using callipers. Once the tumours had reached an average volume of 250 mm³ calculated from the geometric mean diameter using the equation tumour volume=(W*H*L/2), animals were randomly distributed into two groups (n=3): (i) 1-$CaO_2$ NPs and (ii) vehicle only. Following induction of anaesthesia via intraperitoneal injection of Hyponym/Hypnovel (150 µl i.p) of a mixture of 2:1:1; PBS: Hypnorm (0.315 mg/ml fentanyl citrate and fluanisone 10 mg/ml, VetaPharma Ltd, U.K.): Hypnovel (10 mg/ml midazolom, Roche, UK) the oxygen partial pressure ($pO_2$) of tumours was recorded using an Oxylite oxygen electrode sensor. A fibre optic probe was inserted into a 21-gauge needle before insertion into the centre of the tumour tissue. The needle was withdrawn and the probe readings allowed to stabilise for 5 minutes. The oxygen level in the tumours was recorded every second for 20 min. 100 µL aliquots of 1-$CaO_2$ NPs in a PBS vehicle (2 mg/mL) or PBS alone were administered to the respective groups by tail-vein injection with $pO_2$ recorded every second for a further 40 minutes. This time period was chosen to avoid the need for re-administering anaesthesia.

The results are shown in FIG. 8 and reveal no significant change in the $pO_2$ reading in the 20 min period before injection for either group with a mean $pO_2$ reading of ~2.0 mm Hg. However, approximately 10 min after injection, tumour $pO_2$ levels in the 1-$CaO_2$ NP group increased dramatically reaching a peak of 16 mmHg before levelling off at ~6 mm Hg 30 min after injection. In contrast, mice treated with vehicle alone showed no noticeable change in tumour $pO_2$ over the time course of the experiment.

Example 8—Effect of Polymer Coated $CaO_2$ NPs on PDT Efficacy In Vivo

All animals employed in this study were treated humanely and in accordance with licenced procedures under the UK Animals (Scientific Procedures) Act 1986. Mia-PaCa 2 xenograft tumours were established as described above. Once the tumours had reached an average volume of 254±17 $mm^3$ the mice were randomly separated into 4 groups (n=5). Group 1 involved untreated animals, group 2 the PDT only group, Group 3 the 1-$CaO_2$ NPs only group and group 4 the PDT+1-$CaO_2$ NPs group. For group 2, mice received an intratumoural injection (100 µL) of Rose Bengal (0.1 mg/mL) in a PBS solvent and the tumour was then exposed to a LED emitting white light for 3 min (0.05 $J/cm^2$). Group 3 received a tail vein injection (100 µL) of 1-$CaO_2$ NPs in a PBS vehicle (2 mg/mL) while group 4 also received a tail vein injection (100 µL) of 1-$CaO_2$ NPs in a PBS vehicle (2 mg/mL) in addition to an intratumoural injection (100 µL) of Rose Bengal (0.1 mg/mL) and light exposure as described for group 2. The tumour volume was measured daily over the course of 6 days using callipers.

The results for tumour volume are shown in FIG. 9a. The results demonstrate that there was no significant difference in tumour volume for mice treated with PDT alone or with 1-$CaO_2$ NPs alone 5 days after treatment, relative to the untreated control animals. In contrast, a significant reduction (p<0.0005) of 70.5% was observed for animals treated with the 1-$CaO_2$ NPs and PDT over the same time period. In addition, there was no significant change in body weight in animals treated with the 1-$CaO_2$ NPs alone or in combination with PDT suggesting the treatment was well tolerated (FIG. 9b).

These results highlight the benefit of 1-$CaO_2$ NPs in improving the PDT-mediated treatment of hypoxic tumours such as pancreatic adenocarcinoma. The same approach would be expected to enhance other therapies that depend on ROS generation to provide a therapeutic effect, such as SDT and radiotherapy.

The invention claimed is:

1. A method of adjuvant therapy of hypoxic tumour cells or tissues, said method comprising the step of administering to said cells or tissues of a patient in need thereof an amount of $CaO_2$ nanoparticles effective to improve oxygenation in the environment of the hypoxic cells or tissues and enhance a cancer therapy, wherein said $CaO_2$ nanoparticles have a pH-responsive coating obtained by polymerisation of methyl methacrylate, ethyl acrylate and 2-(dimethylamino) ethyl methacrylate.

2. The method as claimed in claim 1, wherein said method is used as an adjuvant therapy to at least one of the following cancer therapies: photodynamic therapy, sonodynamic therapy and radiotherapy.

3. The method as claimed in claim 1, wherein said $CaO_2$ nanoparticles have a diameter of up to about 1 µm.

4. The method as claimed in claim 1, wherein said $CaO_2$ nanoparticles contain at least 10 wt. % of active $CaO_2$ based on the total weight of the particles.

5. The method as claimed in claim 1, wherein said $CaO_2$ nanoparticles consist essentially of calcium peroxide.

6. The method as claimed in claim 1, wherein said $CaO_2$ nanoparticles have a pH-responsive coating which is stable at physiological pH but which degrades at a pH which is less than physiological pH.

7. The method as claimed in claim 6, wherein said pH-responsive coating degrades in the range of pH 6.0 to 7.4.

8. The method as claimed in claim 6, wherein said pH-responsive coating degrades in the range of pH 6.2 to 7.4.

9. The method as claimed in claim 1, wherein said pH-responsive coating comprises a terpolymer having the following structure:

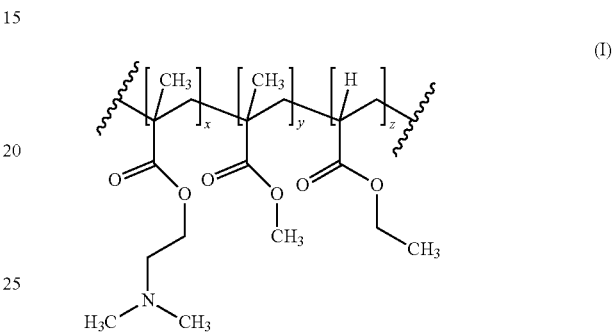

(I)

wherein x, y and z are integers representing the molar ratio of the monomeric units in the polymer material.

10. The method as claimed in claim 1, wherein said pH-responsive coating is linked to one or more of the following active agents: a photosensitiser, a sonosensitiser, a radiosensitiser, or an enzyme capable of catalysing the degradation of hydrogen peroxide to oxygen.

11. The method as claimed in claim 10, wherein said enzyme capable of catalysing the degradation of hydrogen peroxide to oxygen is catalase.

12. The method as claimed in claim 1, wherein said $CaO_2$ nanoparticles are embedded in a polymeric matrix comprising a physiologically acceptable, biodegradable polymer.

13. The method as claimed in claim 12, wherein said physiologically acceptable, biodegradable polymer is poly (D,L-lactide-co-glycolide) (PLGA).

14. The method as claimed in claim 12, wherein said polymeric matrix further comprises one or more of the following active agents: a photosensitiser, a sonosensitiser, a radiosensitiser, or an enzyme capable of catalysing the degradation of hydrogen peroxide to oxygen.

15. The method as claimed in claim 14, wherein said enzyme capable of catalysing the degradation of hydrogen peroxide to oxygen is catalase.

16. The method as claimed in claim 1, wherein said $CaO_2$ nanoparticles have a diameter from 5 to 900 nm.

17. The method as claimed in claim 1, wherein said $CaO_2$ nanoparticles contain at least 25 wt. % of active $CaO_2$ based on the total weight of the particles.

18. The method as claimed in claim 1, wherein said $CaO_2$ nanoparticles have a pH-responsive coating which is stable at physiological pH but which degrades at a pH of less than 7.4.

19. A method of treatment of hypoxic tumour cells or tissues, said method comprising the following steps:
(i) administering to said cells or tissues of a patient in need thereof an amount of $CaO_2$ nanoparticles effective to improve oxygenation in the environment of the hypoxic cells or tissues, wherein said $CaO_2$ nanoparticles have a pH-responsive coating obtained by polymerisation of methyl methacrylate, ethyl acrylate and 2-(dimethylamino)ethyl methacrylate;

(ii) administering to said cells or tissues of said patient at least one of the following active agents: a photosensitizer, a sonosensitizer, or a radiosensitizer; and (iii) subjecting said cells or tissues to one or more of the following: light, ultrasound and ionising radiation whereby to treat said tumour cells or tissues.

20. The method as claimed in claim 19, wherein said steps are carried out in the following order: (ii), (i), (iii).

* * * * *